(12) United States Patent
Sommerlade

(10) Patent No.: US 11,203,580 B2
(45) Date of Patent: Dec. 21, 2021

(54) SIMPLE OXIDATIVE FUNCTIONALIZED OF ALKYL ARYL KETONES

(71) Applicant: IGM GROUP B.V., Waalwijk (NL)

(72) Inventor: Reinhard Sommerlade, Neuenburg am Rhein (DE)

(73) Assignee: IGM GROUP B.V., Waalwijk (NL)

( * ) Notice: Subject to any disclaimer, the term of this patent is extended or adjusted under 35 U.S.C. 154(b) by 119 days.

(21) Appl. No.: 16/603,534

(22) PCT Filed: Apr. 19, 2018

(86) PCT No.: PCT/EP2018/060011
§ 371 (c)(1),
(2) Date: Oct. 7, 2019

(87) PCT Pub. No.: WO2018/197324
PCT Pub. Date: Nov. 1, 2018

(65) Prior Publication Data
US 2020/0031790 A1   Jan. 30, 2020

(30) Foreign Application Priority Data

Apr. 24, 2017 (EP) ..................... 17167816

(51) Int. Cl.
| C07D 301/02 | (2006.01) |
| C07C 41/56 | (2006.01) |
| C07C 43/315 | (2006.01) |
| C07D 265/30 | (2006.01) |
| C07D 303/02 | (2006.01) |
| C07C 49/84 | (2006.01) |

(52) U.S. Cl.
CPC ............ *C07D 301/02* (2013.01); *C07C 41/56* (2013.01); *C07C 43/315* (2013.01); *C07D 265/30* (2013.01); *C07D 303/02* (2013.01); *C07C 49/84* (2013.01)

(58) Field of Classification Search
CPC .. C07D 301/02; C07D 265/30; C07D 303/02; C07D 295/108; C07C 41/56; C07C 43/315; C07C 49/84
USPC ........................................ 549/519
See application file for complete search history.

(56) References Cited

U.S. PATENT DOCUMENTS

| 4,740,624 A | 4/1988 | Kohler et al. |
| 2015/0329662 A1 | 11/2015 | Song et al. |

FOREIGN PATENT DOCUMENTS

| CN | 101624321 A |   | 1/2010 |
| CN | 101724099 A | * | 6/2010 |
| DE | 2722264 C2 |   | 6/1984 |
| JP | 57050956 A |   | 3/1982 |
| JP | 57098232 A |   | 6/1982 |
| JP | 57192325 A |   | 11/1982 |
| JP | 01221349 A |   | 9/1989 |
| JP | 64070431 A |   | 3/1999 |
| JP | 2008514671 A |   | 5/2008 |
| JP | 2013538243 A |   | 10/2013 |
| JP | 2016512842 A |   | 5/2016 |
| WO | 2006/034966 A1 |   | 4/2006 |
| WO | 2011001928 A1 |   | 1/2011 |
| WO | 2014/151409 A1 |   | 9/2014 |

OTHER PUBLICATIONS

E. Abele et al, Synthetic Communications, Simple Phase Transfer Catalytic Method for α-Methoxylation of Sterically Hindered KetonesSynthetic Communications, 25(9), p. 1371-1376). (Year: 1995).*
Aneja, et al. "Synthesis of Beno-Furan Derivatives-I", Tetrahedron, 1958, vol. 2, pp. 203-210, Pergamon Press Ltd., London.
Chen, et al., "α-Hydroxylation of Enolates and Silyl Enol Ethers", Organic Reactions, vol. 62, 2003.
Chen, et al., "An Efficient Method for the Synthesis of a-Hydroxyalkyl Aryl Ketones", Synthesis 2008, No. 20, pp. 3205-3208.y Carbonyl Compounds, J. Org. Chem. 1987,52, 954-955.
Davis, et al., "Oxidation of Silyl Enol Ethers Using 2-Sulfonyloxaziridines. Synthesis of a-Siloxy Epoxides and a-Hydroxy Carbonyl Compounds", J. Org. Chem. 1987, 52, 954-955.
Chuang, et al., "A Dinuclear Palladium Catalyst for r-Hydroxylation of Carbonyls with O2", J. Am. Chem. Soc. 2011, 133, 1760-1762.
Kattenberg, et al., "Chlorination of a-Sulfonyl Carbanions With Hexachloroethane a", Tetrahedron—vol. 29, May 1, 1974, pp. 4149-4152.
Jain, et al., "Synthesis of Isopentenyiated 4-Hydroxy_3_Methoxycoumarins and W_Methyl_w_Desacetyl Ripariochromene-B", Synthetic Communications, 6,2, 147-166, 1976.
Koprowski et al., "Asymmetric oxidation of enol phosphates to a-hydroxy ketones by salen manganese III complex. Effects of the substitution pattern of enol phosphates on the stereochemistry of oxygen transfer", Tetrahedron 62, 2006, 12363-12374.
Liang, et al., "I2- or NBS-Catalyzed Highly Efficient a-Hydroxylation of Ketones with Dimethyl Sulfoxide", Org. Lett. 2015, 17, 876-879.
Liang, et al., "Highly Efficient CH Hydroxylation of Carbonyl Compounds with Oxygen under Mild Conditions", Angew. Chem. 2014, 126, 558-562.
Applicant: IGM Group B.V; Japanese Patent Application No. 2019-554980; Japanese Office Action dated Nov. 13, 2020; 6 pgs.

\* cited by examiner

*Primary Examiner* — Taylor V Oh
(74) *Attorney, Agent, or Firm* — Tarolli, Sundheim, Covell & Tummino LLP

(57) ABSTRACT

The present invention refers to a process for reacting an alkyl aryl ketone obtaining thereby the corresponding aryl oxirane or α-functionalized alkyl aryl ketal, the aryl oxirane or α-functionalized alkyl aryl ketal obtained by the process as well as the α-functionalized ketone obtained by the process.

22 Claims, No Drawings

SIMPLE OXIDATIVE FUNCTIONALIZED OF ALKYL ARYL KETONES

FIELD OF THE INVENTION

The present invention refers to a process for reacting an alkyl aryl ketone obtaining thereby the corresponding aryl oxirane or α-functionalized alkyl aryl ketal, the aryl oxirane or α-functionalized alkyl aryl ketal obtained by the process as well as the α-functionalized ketone obtained by the process.

BACKGROUND OF THE INVENTION

Photopolymerization processes have attained major importance in a large number of applications, for example in overprint coatings, printing inks, in the manufacture of electronic printed circuit boards and printing plates, and in the coating of various substrates, such as wood, plastics, paper, glass or metal, due their tremendous advantages over conventional hardening systems. One advantage of photocuring by UV irradiation in the presence of photoinitiators is the great speed. However, the speed is heavily dependent on the photoinitiator used. Among the most effective photoinitiators are α-hydroxylated ketones as described e.g. in German Patent No. 2,722,264 and U.S. Pat. No. 4,740,624. Further methods for the α-functionalization of ketones are described e.g. in Gary Jing Chuang et al., "A Dinuclear Palladium Catalyst for α-Hydroxylation of Carbonyls with $O_2$", J. Am. Chem. Soc. 133, 1760-1762 (2011). Chengqun Chen et al. "An Efficient Method for the Synthesis of α-Hydroxyalkyl Aryl Ketones", Synthesis 2008, No. 20, 3205-3208; Marek Koprowski et al., "Asymmetric oxidation of enol phosphates to α-hydroxy ketones by (salen)manganese(III) complex; Effects of the substitution pattern of enol phosphates on the stereochemistry of oxygen transfer", Tetrahedron 62 12363-12374 (2006); Franklin A. Davis et al., "Oxidation of Silyl Enol Ethers Using 2-Sulfonyloxaziridines; Synthesis of α-Siloxy Epoxides and α-Hydroxy Carbonyl Compounds", J. Org. Chem. 52, 954-955 (1987); Yu-Feng Liang et al., "Highly Efficient C—H Hydroxylation of Carbonyl Compounds with Oxygen under Mild Conditions", Angew. Chem. 2014, 126, 558-562; Yu-Feng Liang et al., "$I_2$- or NBS-Catalyzed Highly Efficient aHydroxylation of Ketones with Dimethyl Sulfoxide", Org. Lett. 17, 876-879 (2015); Bang-Chi Chen et al., "α-hydroxylation of enolates and silyl enol ethers", Organic Reactions, Vol. 62, 2003, published by John Wiley & Sons, Inc.

However, the processes used for the preparation of α-hydroxylated ketones show a number of disadvantages. In particular, it is to be noted that the α-hydroxylated ketones are prepared by complex reactions resulting in a great variety of unwanted intermediate products and by-products which reduce the yield and purity of the desired α-hydroxylated ketone and which are of no commercial interest. Furthermore, often elaborate purification steps are required. Accordingly, the well-known processes of the prior art are quite complex as well as time- and chemical-consuming.

Therefore, there is a continuous need in the art for providing a process for the preparation of α-functionalized ketones avoiding the forgoing disadvantages. Furthermore, it is desirable to provide a process for the preparation of α-functionalized ketones which uses cheap starting materials. Furthermore, it is desirable to provide a process for the preparation of α-functionalized ketones which avoids complex processing and elaborate purification steps for obtaining the desired α-functionalized ketones. In addition thereto, it is desirable to provide a process for the preparation of α-functionalized ketones which avoids the formation of unwanted by-products and thus increases the yield and purity of the desired α-functionalized ketones. Furthermore, it is desirable to provide a process which allows the preparation of defined intermediate products, such as alkyl aryl ketals and/or aryl oxiranes.

Accordingly, it is an object of the present invention to provide a process for the preparation of α-functionalized ketones. It is an even further object of the present invention to provide a process for the preparation of α-functionalized ketones using cheap starting materials and without complex processing or elaborate purification steps for obtaining the desired α-functionalized ketones. It is an even further object of the present invention to provide a process for the preparation of α-functionalized ketones which increases the yield and purity of the desired α-functionalized ketones. It is another object of the present invention to provide a process which allows the preparation of defined intermediate products, such as alkyl aryl ketals and/or aryl oxiranes.

SUMMARY OF THE INVENTION

The foregoing and other objects are solved by the subject-matter of the present invention.

According to a first aspect of the present invention, a process for reacting an alkyl aryl ketone of the general formula I,

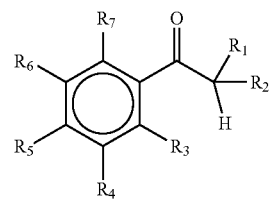

wherein $R_1$ and $R_2$ are the same or different and are independently selected from H, linear or branched $C_1$-$C_8$-alkyl, $C_3$-$C_8$-cycloalkyl, linear or branched $C_2$-$C_8$-alkenyl, $C_5$-$C_8$-cycloalkenyl, linear or branched $C_2$-$C_8$-alkynyl, $C_6$-$C_{14}$-aryl or form $C_3$-$C_{12}$-cycloalkyl or $C_5$-$C_{12}$-cycloalkenyl together with the connecting C atom;

$R_3$, $R_4$, $R_5$, $R_6$ and $R_7$ are the same or different and are independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_6$-$C_{14}$-aryl, $C_3$-$C_8$-cycloalkoxy, $C_7$-$C_{15}$-arylalkoxy, $C_9$-$C_{15}$-alkenylarylalkoxy, $N(R_8)_2$ or $SR_8$ with $R_8$ being selected from linear or branched $C_1$-$C_8$-alkyl, linear or branched $C_2$-$C_8$-alkenyl, $C_6$-$C_{14}$-aryl, $C_1$-$C_8$-alkoxy, $C_2$-$C_8$-alkenyloxy, $C_3$-$C_8$-cycloalkyl, $C_3$-$C_8$-cycloalkoxy, $C_7$-$C_{15}$-arylalkoxy, $C_9$-$C_{15}$-alkenylarylalkoxy, or $R_8$ form a $C_3$-$C_9$-alicyclic system together with the connecting N atom, optionally one or more carbon atoms are replaced with O, or two adjacent R form an aromatic system together with the benzene ring of formula I;

with an at least partially halogenated $C_2$-$C_8$-alkane and/or $C_2$-$C_8$-alkene, and a base selected from alkali metal $C_1$-$C_8$-alkoxide, earth alkali metal $C_1$-$C_8$-alkoxide and mixtures thereof, obtaining thereby the corresponding aryl oxirane or α-functionalized alkyl aryl ketal.

The inventors surprisingly found out that such a process is suitable for the preparation of α-functionalized ketones by the use of cheap starting materials and which avoids complex processing and elaborate purification steps for obtaining the desired α-functionalized ketones. The process thus increases the yield and purity of the desired α-functionalized ketones. Furthermore, the process allows the preparation of defined intermediate products, i.e. aryl oxiranes and α-functionalized alkyl aryl ketals, which are of commercial interest.

Advantageous embodiments of the inventive process are defined in the corresponding sub-claims.

According to one embodiment, $R_1$ and $R_2$ are the same.

According to another embodiment, $R_1$ and $R_2$ are selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl.

According to yet another embodiment, $R_1$ and $R_2$ are different and are independently selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl.

According to one embodiment, $R_1$ and $R_2$ form $C_4$-$C_{10}$-cycloalkyl, preferably $C_4$-$C_8$-cycloalkyl, and most preferably $C_6$-cycloalkyl, together with the connecting C atom.

According to another embodiment, $R_3$, $R_4$, $R_5$, $R_6$ and $R_7$ are the same. According to yet another embodiment, $R_3$, $R_4$, $R_5$, $R_6$ and $R_7$ are selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl.

According to one embodiment, $R_3$, $R_4$, $R_5$, $R_6$ and $R_7$ are different and at least one of them is selected from linear or branched $C_1$-$C_8$-alkyl, linear or branched $C_2$-$C_8$-alkenyl, $C_1$-$C_8$-alkoxy, $C_2$-$C_8$-alkenyloxy, $C_9$-$C_{15}$-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom.

According to another embodiment, one of $R_3$, $R_4$, $R_5$, $R_6$ and $R_7$ is linear or branched $C_2$-$C_8$-alkenyl, preferably $C_2$-$C_6$-alkenyl and most preferably $C_2$-$C_3$-alkenyl; $C_1$-$C_8$-alkoxy, preferably $C_1$-$C_6$-alkoxy and most preferably $C_1$-$C_3$-alkoxy; $C_2$-$C_8$-alkenyloxy, preferably $C_2$-$C_6$-alkenyloxy and most preferably $C_3$-$C_5$-alkenyloxy; $C_9$-$C_{15}$-alkenylarylalkoxy, preferably $C_9$-$C_{12}$-alkenylarylalkoxy and most preferably $C_9$-$C_{10}$-alkenylarylalkoxy; or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom; and the remaining ones are independently selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl.

According to yet another embodiment, two or three of $R_3$, $R_4$, $R_5$, $R_6$ and $R_7$ are linear or branched $C_2$-$C_8$-alkenyl, preferably $C_2$-$C_6$-alkenyl and most preferably $C_2$-$C_3$-alkenyl; $C_1$-$C_8$-alkoxy, preferably $C_1$-$C_6$-alkoxy and most preferably $C_1$-$C_3$-alkoxy; $C_2$-$C_8$-alkenyloxy, preferably $C_2$-$C_6$-alkenyloxy and most preferably $C_3$-$C_0$-alkenyloxy; and $C_9$-$C_{15}$-alkenylarylalkoxy, preferably $C_9$-$C_{12}$-alkenylarylalkoxy and most preferably $C_9$-$C_{10}$-alkenylarylalkoxy, and the remaining ones are independently selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl.

According to one embodiment, $R_3$ and $R_4$ or $R_4$ and $R_5$ form an aromatic system together with the benzene ring of formula I, preferably a bicyclic, tricyclic or tetracyclic aromatic system, more preferably an aromatic system selected from a naphthyl, anthracenyl and phenanthrenyl system.

According to another embodiment, one of the remaining R is linear or branched $C_2$-$C_8$-alkenyl, preferably $C_2$-$C_6$-alkenyl and most preferably $C_2$-$C_3$-alkenyl; $C_2$-$C_8$-alkenyloxy, preferably $C_2$-$C_6$-alkenyloxy and most preferably $C_3$-$C_5$-alkenyloxy; and $C_9$-$C_{15}$-alkenylarylalkoxy, preferably $C_9$-$C_{12}$-alkenylarylalkoxy and most preferably $C_9$-$C_{10}$-alkenylarylalkoxy; and the remaining ones are independently selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl.

According to yet another embodiment, the at least partially halogenated $C_2$-$C_8$-alkane and/or $C_2$-$C_8$-alkene is fully halogenated, preferably the at least partially halogenated $C_2$-$C_8$-alkane and/or $C_2$-$C_8$-alkene is selected from hexachloroethane, tetrachoroethylene and mixtures thereof.

According to one embodiment, the base is selected from the group comprising sodium $C_1$-$C_6$-alkoxide, preferably sodium $C_1$-$C_4$-alkoxide and most preferably sodium $C_1$-$C_2$-alkoxide; lithium $C_1$-$C_6$-alkoxide, preferably lithium $C_1$-$C_4$-alkoxide and most preferably lithium $C_1$-$C_2$-alkoxide; potassium $C_1$-$C_6$-alkoxide, preferably potassium $C_1$-$C_4$-alkoxide and most preferably potassium $C_1$-$C_2$-alkoxide; and mixtures thereof.

According to another embodiment, the base is in form of an aqueous solution or the base is provided in an organic solvent, preferably the organic solvent is selected from the group comprising methanol, ethanol, n-propanol, tert.-butanol, dichloromethane, tetrachloroethylene, tetrahydrofuran, ethyl acetate, acetone, N,N-dimethylformamide, dimethyl sulfoxide, dioxane, such as 1,3-dioxane or 1,4-dioxane, 1,2-dimethoxyethane, diethyleneglycol dimethyl ether, triethyleneglycol dimethyl ether and mixtures thereof.

According to yet another embodiment, the process is carried out at a temperature in the range from 0 to 120° C., preferably in the range from 12 to 80° C., more preferably in the range from 15 to 50° C., and most preferably in the range from 15 to 30° C.

According to one embodiment, the process is carried out in an organic solvent, preferably the organic solvent is selected from the group comprising methanol, ethanol, n-propanol, tert.-butanol, dichloromethane, tetrachloroethylene, tetrahydrofuran, ethyl acetate, acetone, N,N-dimethylformamide, dimethyl sulfoxide, dioxane, such as 1,3-dioxane or 1,4-dioxane, 1,2-dimethoxyethane, diethyleneglycol dimethyl ether, triethyleneglycol dimethyl ether and mixtures thereof.

According to one embodiment, the process comprises a further step of contacting the aryl oxirane obtained by the process under phase-transfer conditions with a base selected from the group comprising alkali metal hydroxide, earth alkali metal hydroxide, alkali metal $C_1$-$C_8$-alkoxide, earth alkali metal $C_1$-$C_8$-alkoxide and mixtures and a compound selected from $HOR_9$, $HNHR_9$ or $HNR_{10}R_{11}$ with $R_9$, $R_{10}$ and $R_{11}$ being independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_6$-$C_{14}$-aryl, $C_7$-$C_{15}$-arylalkyl, $C_7$-$C_{15}$-arylalkoxy, $C_9$-$C_{15}$-alkenylarylalkoxy, $C_9$-$C_{15}$-alkenylarylalkyl; or $R_{10}$ and $R_{11}$ form a $C_3$-$C_9$-alicyclic system together with the connecting N or C atom, optionally one or more carbon atoms are replaced with O.

According to another embodiment, the step is carried out in the presence of a phase-transfer catalyst, preferably the phase-transfer catalyst is selected from a quaternary ammonium salt, tetraalkylphosphonium chloride, tetraalkylphosphonium bromide and mixtures thereof, preferably the phase-transfer catalyst is a tetraalkylammonium salt or a trialkylarylammonium salt, more preferably the phase-transfer catalyst is selected from the group comprising benzyltrimethylammonium hydroxide, benzyltriethylammonium chloride, tetrabutylammonium chloride, tetrabutylammonium bromide, tetrabutylammonium hydrogensulfate, tetrabutylammonium hydroxide, methyltrioctylammonium chloride, cetyl pyridinium and mixtures thereof.

According to yet another embodiment, the process comprises a further step of contacting the α-functionalized alkyl aryl ketal obtained by the process with an acid, preferably an acid selected from the group comprising hydrochloric acid, acetic acid, phosphoric acid, sulfuric acid, citric acid, toluenesulfonic acid, methanesulfonic acid, chloroacetic acid, trichloroacetic acid, tartaric acid, succinic acid, maleic acid, fumaric acid, lactic acid, malic acid, propionic acid, butyric acid and mixtures thereof.

According to one embodiment, an α-functionalized ketone of the general formula II is obtained,

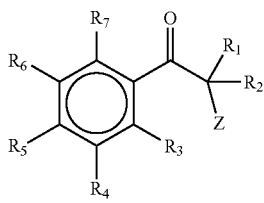

II wherein $R_1$, $R_2$, $R_3$, $R_4$, $R_5$, $R_6$ and $R_7$ are as defined above; and Z is selected from $OR_9$, $NHR_9$ and $NR_{10}R_{11}$ with $R_9$, $R_{10}$ and $R_{11}$ being independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_6$-$C_{14}$-aryl, $C_7$-$C_{15}$-arylalkyl, $C_7$-$C_{15}$-arylalkoxy, $C_9$-$C_{15}$-alkenylarylalkoxy, $C_9$-$C_{15}$-alkenylarylalkyl; or $R_{10}$ and $R_{11}$ form a $C_3$-$C_9$-alicyclic system together with the connecting N or C atom, optionally one or more carbon atoms are replaced with O.

According to another embodiment, Z is $OR_9$ with $R_9$ being selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_7$-$C_{15}$-arylalkoxy and $C_9$-$C_{15}$-alkenylarylalkoxy, preferably $R_9$ is H or Z is $NR_{10}R_{11}$ with $R_{10}$ and $R_{11}$ being independently selected from H, linear or branched $C_1$-$C_8$-alkyl, $C_3$-$C_8$-cycloalkyl, $C_6$-$C_{14}$-aryl, or $R_{10}$ and $R_{11}$ form a $C_3$-$C_6$-alicyclic system together with the connecting N atom, optionally one or more carbon atoms are replaced with O, preferably $R_{10}$ and $R_{11}$ form a $C_5$-$C_6$-alicyclic system together with the connecting N atom and one or more carbon atoms are replaced with O.

According to a further aspect of the present invention, an aryl oxirane or α-functionalized alkyl aryl ketal obtained by a process, as defined herein, is provided. According to another aspect of the present invention, an α-functionalized ketone obtained by a process as defined herein, is provided.

In the following, the details and preferred embodiments of the inventive process for reacting an alkyl aryl ketone will be described in more detail. It is to be understood that these technical details and embodiments also apply to the inventive products, as far as applicable.

DETAILED DESCRIPTION OF THE INVENTION

A process for reacting an alkyl aryl ketone is provided. In particular, a process for reacting an alkyl aryl ketone of the general formula I,

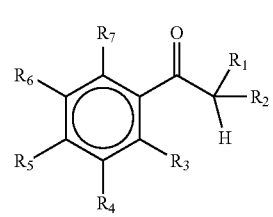

I wherein $R_1$ and $R_2$ are the same or different and are independently selected from H, linear or branched $C_1$-$C_8$-alkyl, $C_3$-$C_8$-cycloalkyl, linear or branched $C_2$-$C_8$-alkenyl, $C_5$-$C_8$-cycloalkenyl, linear or branched $C_2$-$C_8$-alkynyl, $C_6$-$C_{14}$-aryl or form $C_3$-$C_{12}$-cycloalkyl or $C_5$-$C_{12}$-cycloalkenyl together with the connecting C atom;

$R_3$, $R_4$, $R_5$, $R_6$ and $R_7$ are the same or different and are independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_6$-$C_{14}$-aryl, $C_3$-$C_8$-cycloalkoxy, $C_7$-$C_{15}$-arylalkoxy, $C_9$-$C_{15}$-alkenylarylalkoxy, $N(R_8)_2$ or $SR_8$ with $R_8$ being selected from linear or branched $C_1$-$C_8$-alkyl, linear or branched $C_2$-$C_8$-alkenyl, $C_6$-$C_{14}$-aryl, $C_1$-$C_8$-alkoxy, $C_2$-$C_8$-alkenyloxy, $C_3$-$C_8$-cycloalkyl, $C_3$-$C_8$-cycloalkoxy, $C_7$-$C_{15}$-arylalkoxy, $C_9$-$C_{15}$-alkenylarylalkoxy, or $R_8$ form a $C_3$-$C_9$-alicyclic system together with the connecting N atom, optionally one or more carbon atoms are replaced with O, or two adjacent R form an aromatic system together with the benzene ring of formula I;

with an at least partially halogenated $C_2$-$C_8$-alkane and/or $C_2$-$C_8$-alkene, and a base selected from alkali metal $C_1$-$C_8$-alkoxide, earth alkali metal $C_1$-$C_8$-alkoxide and mixtures thereof, obtaining thereby the corresponding aryl oxirane or α-functionalized alkyl aryl ketal, is provided.

Thus, it is appreciated that an alkyl aryl ketone of the general formula I is used as starting material,

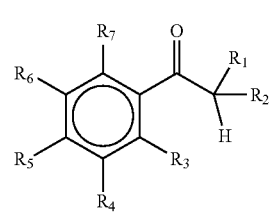

I wherein $R_1$ and $R_2$ are the same or different and are independently selected from H, linear or branched $C_1$-$C_8$-alkyl, $C_3$-$C_8$-cycloalkyl, linear or branched $C_2$-$C_8$-alkenyl, $C_5$-$C_8$-cycloalkenyl, linear or branched $C_2$-$C_8$-alkynyl, $C_6$-$C_{14}$-aryl, or form $C_3$-$C_{12}$-cycloalkyl or $C_5$-$C_{12}$-cycloalkenyl together with the connecting C atom;

$R_3$, $R_4$, $R_5$, $R_6$ and $R_7$ are the same or different and are independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_6$-$C_{14}$-aryl, $C_3$-$C_8$-cycloalkoxy, $C_7$-$C_{15}$-arylalkoxy, $C_9$-$C_{15}$-alkenylarylalkoxy, $N(R_8)_2$ or $SR_8$ with $R_8$ being selected from linear or branched $C_1$-$C_8$-alkyl, linear or branched $C_2$-$C_8$-alkenyl, $C_6$-$C_{14}$-aryl, $C_1$-$C_8$-alkoxy, $C_2$-$C_8$-alkenyloxy, $C_3$-$C_8$-cycloalkyl, $C_3$-$C_8$-cycloalkoxy, $C_7$-$C_{15}$-arylalkoxy, $C_9$-$C_{15}$-alkenylarylalkoxy, or $R_8$ form a $C_3$-$C_9$-alicyclic system together with the connecting N atom, optionally one or more carbon atoms are replaced with O, or two adjacent R form an aromatic system together with the benzene ring of formula I.

As regards $R_1$ and $R_2$ in the general formula I, it is to be noted that they can be the same or different. Preferably, $R_1$ and $R_2$ are the same or different and are independently selected from H, linear or branched $C_1$-$C_8$-alkyl, $C_3$-$C_8$-cycloalkyl, linear or branched $C_2$-$C_8$-alkenyl, $C_5$-$C_8$-cycloalkenyl, linear or branched $C_2$-$C_8$-alkynyl, $C_6$-$C_{14}$-aryl or form $C_3$-$C_{12}$-cycloalkyl or $C_5$-$C_{12}$-cycloalkenyl together with the connecting C atom.

The term "linear or branched $C_1$-$C_8$-alkyl" in the meaning of the present invention refers to a linear or branched chain alkyl group having 1 to 8 carbon atoms, and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl and 1,1,3,3-tetramethylbutyl.

The term "$C_3$-$C_8$-cycloalkyl" in the meaning of the present invention refers to a cyclic alkyl having 3 to 8 carbon atoms, and includes, for example, cyclopropyl, cyclobutyl, cyclopentyl, cyclohexyl, and cycloheptyl.

The term "$C_5$-$C_8$-cycloalkenyl" in the meaning of the present invention refers to a cyclic alkenyl having 3 to 8 carbon atoms, and includes, for example, cyclopentenyl, cyclohexenyl, and cycloheptenyl.

The term "linear or branched $C_2$-$C_8$-alkenyl" in the meaning of the present invention refers to a linear or branched chain alkenyl group having 2 to 8 carbon atoms, and includes, for example, ethenyl, propenyl such as 2-propenyl, butenyl, triisobutenyl, pentenyl, hexenyl, heptenyl and octenyl. The term "alkenyl" in the meaning of the present invention includes the cis and trans isomers.

The term "linear or branched $C_2$-$C_8$-alkynyl" in the meaning of the present invention refers to a linear or branched chain alkynyl group having 2 to 8 carbon atoms, and includes, for example, ethynyl, propynyl such as 1-propynyl or 2-propynyl, e.g. propargyl, butynyl, pentynyl, hexynyl, heptynyl and octynyl.

The term "$C_6$-$C_{14}$-aryl" in the meaning of the present invention refers to a group containing one or more 6-membered unsaturated hydrocarbon ring(s), wherein the unsaturation is represented formally by conjugated double bonds and which may optionally be substituted at one or more carbon atoms of such ring(s) by independently selected alkyl groups. Thus, the term "$C_6$-$C_{14}$-aryl" preferably includes (unsubstituted) $C_6$-$C_{10}$-aryl and $C_6$-$C_{14}$-alkylaryl. Suitable examples include, for example, phenyl, naphthyl, methylphenyl, dimethoxyphenyl, 5-isopropyl-2-methylphenyl, methylphenyl, ethylphenyl, dimethylphenyl, t-butylphenyl, methylnaphthyl and dimethylnaphthyl.

The term "form $C_3$-$C_{12}$-cycloalkyl together with the connecting C atom" in the meaning of the present invention refers to a mono-, bi- or tricyclic alkyl having 3 to 12 carbon atoms, and includes, for example, cyclopropyl, cyclobutyl, cyclopentyl, cyclohexyl, cycloheptyl, norbornyl and adamantyl.

The term "form $C_5$-$C_{12}$-cycloalkenyl together with the connecting C atom" in the meaning of the present invention refers to a mono-, bi- or tricyclic alkenyl having 5 to 12 carbon atoms, and includes, one or more, preferably one, double bond(s). Suitable examples include, for example, cyclopentenyl, cyclohexenyl, cyclohexadienyl and cycloheptenyl. It is appreciated that the double bond of the $C_5$-$C_{12}$-cycloalkenyl is located such that an α,β-unsaturated carbonyl compound is not formed. Thus, $R_1$ and $R_2$ in the general formula I can form $C_5$-$C_{12}$-cycloalkenyl together with the connecting C atom with the proviso that no α,β-unsaturated carbonyl compound is formed.

In one embodiment, $R_1$ and $R_2$ are the same or different and are independently selected from H, linear or branched $C_1$-$C_8$-alkyl, $C_3$-$C_8$-cycloalkyl, or form $C_3$-$C_{12}$-cycloalkyl together with the connecting C atom. Preferably, $R_1$ and $R_2$ are the same or different and are independently selected from H or linear or branched $C_1$-$C_8$-alkyl.

For example, $R_1$ and $R_2$ are the same. In this embodiment, $R_1$ and $R_2$ are preferably selected from H, linear or branched $C_1$-$C_8$-alkyl, $C_3$-$C_8$-cycloalkyl, linear or branched $C_2$-$C_8$-alkenyl, $C_5$-$C_8$-cycloalkenyl, linear or branched $C_2$-$C_8$-alkynyl, $C_6$-$C_{14}$-aryl or form $C_3$-$C_{12}$-cycloalkyl or $C_5$-$C_{12}$-cycloalkenyl together with the connecting C atom.

In one embodiment, $R_1$ and $R_2$ are the same and are H.

In another embodiment, $R_1$ and $R_2$ are the same and are linear or branched $C_1$-$C_8$-alkyl, e.g. linear $C_1$-$C_8$-alkyl. For example, $R_1$ and $R_2$ are the same and are linear or branched $C_1$-$C_6$-alkyl, e.g. linear $C_1$-$C_6$-alkyl, preferably linear or branched $C_1$-$C_4$-alkyl, e.g. linear $C_1$-$C_4$-alkyl, and most preferably linear or branched $C_1$-$C_3$-alkyl, e.g. linear $C_1$-$C_3$-alkyl. It is especially preferred that $R_1$ and $R_2$ are the same and are $C_1$- or $C_2$-alkyl, e.g. $C_1$-alkyl.

In another embodiment, $R_1$ and $R_2$ form $C_3$-$C_{12}$-cycloalkyl together with the connecting C atom. For example, $R_1$ and $R_2$ form $C_4$-$C_{10}$-cycloalkyl, preferably $C_4$-$C_8$-cycloalkyl, more preferably $C_4$-$C_6$-cycloalkyl, and most preferably $C_5$- or $C_6$-cycloalkyl, e.g. $C_6$-cycloalkyl, together with the connecting C atom.

In another embodiment, $R_1$ and $R_2$ are the same and are linear or branched $C_2$-$C_8$-alkenyl, e.g. linear $C_2$-$C_8$-alkenyl. For example, $R_1$ and $R_2$ are the same and are linear or branched $C_2$-$C_6$-alkenyl, e.g. linear $C_2$-$C_6$-alkenyl, preferably linear or branched $C_2$-$C_4$-alkenyl, e.g. linear $C_2$-$C_4$-alkenyl, and most preferably linear or branched $C_2$- or $C_3$-alkenyl, e.g. linear $C_2$- or $C_3$-alkenyl. It is especially preferred that $R_1$ and $R_2$ are the same and are $C_3$-alkenyl.

In another embodiment, $R_1$ and $R_2$ are the same and are linear or branched $C_2$-$C_8$-alkynyl, e.g. linear $C_2$-$C_8$-alkynyl. For example, $R_1$ and $R_2$ are the same and are linear or branched $C_2$-$C_6$-alkynyl, e.g. linear $C_2$-$C_6$-alkynyl, preferably linear or branched $C_2$-$C_4$-alkynyl, e.g. linear $C_2$-$C_4$-alkynyl, and most preferably linear or branched $C_2$- or $C_3$-alkynyl, e.g. linear $C_2$- or $C_3$-alkynyl. It is especially preferred that $R_1$ and $R_2$ are the same and are $C_3$-alkynyl.

In another embodiment, $R_1$ and $R_2$ are the same and are linear or branched $C_6$-$C_{14}$-aryl, e.g. (unsubstituted) $C_6$-$C_{10}$-aryl or $C_6$-$C_{14}$-alkylaryl. For example, $R_1$ and $R_2$ are the same and are (unsubstituted) $C_6$- or $C_{10}$-aryl. Alternatively, $R_1$ and $R_2$ are the same and are $C_8$-$C_{12}$-alkylaryl.

In another embodiment, $R_1$ and $R_2$ form $C_5$-$C_{12}$-cycloalkenyl together with the connecting C atom. For example, $R_1$ and $R_2$ form $C_5$-$C_{10}$-cycloalkenyl, preferably $C_5$-$C_8$-cycloalkenyl and most preferably $C_5$- or $C_6$-cycloalkenyl, e.g. $C_6$-cycloalkenyl, together with the connecting C atom.

If $R_1$ and $R_2$ are the same, it is preferred that $R_1$ and $R_2$ are linear or branched $C_1$-$C_8$-alkyl, preferably linear $C_1$-$C_8$-alkyl, or form $C_3$-$C_{12}$-cycloalkyl, preferably $C_5$- or $C_6$-cycloalkyl, together with the connecting C atom. More preferably, $R_1$ and $R_2$ are linear or branched $C_1$-$C_8$-alkyl, preferably linear $C_1$-$C_8$-alkyl, or form $C_3$-$C_{12}$-cycloalkyl. Most preferably, $R_1$ and $R_2$ are linear or branched $C_1$-$C_8$-alkyl, preferably linear $C_1$-$C_8$-alkyl.

Alternatively, $R_1$ and $R_2$ are different. In this embodiment, $R_1$ and $R_2$ are preferably independently selected from H, linear or branched $C_1$-$C_8$-alkyl, $C_3$-$C_8$-cycloalkyl, linear or branched $C_2$-$C_8$-alkenyl, $C_5$-$C_8$-cycloalkenyl, linear or branched $C_2$-$C_8$-alkynyl or $C_6$-$C_{14}$-aryl. For example, $R_1$ and $R_2$ are different and are selected from H, linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, linear or branched $C_2$-$C_8$-alkenyl, e.g. linear $C_2$-$C_8$-alkenyl, preferably linear or branched $C_2$-$C_6$-alkenyl, e.g. linear $C_2$-$C_6$-alkenyl, more preferably linear or branched $C_2$-$C_4$-alkenyl, e.g. linear $C_2$-$C_4$-alkenyl, even more preferably linear or branched $C_2$- or $C_3$-alkenyl, e.g. linear $C_2$- or $C_3$-alkenyl and most preferably $C_3$-alkenyl, and linear or branched $C_2$-$C_8$-alkynyl, e.g. linear $C_2$-$C_8$-alkynyl, preferably linear or branched $C_2$-$C_6$-alkynyl, e.g. linear $C_2$-$C_6$-alkynyl, more preferably linear or branched $C_2$-$C_4$-alkynyl, e.g. linear $C_2$-$C_4$-alkynyl, even more preferably linear or branched $C_2$- or $C_3$-alkynyl, e.g. linear $C_2$- or $C_3$-alkynyl and most preferably $C_3$-alkynyl. In one embodiment, $R_1$ and $R_2$ are different and are selected from H and linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl. In one embodiment, $R_1$ and $R_2$ are different and are selected from H and $C_1$- or $C_2$-alkyl, preferably $C_2$-alkyl.

If $R_1$ and $R_2$ are different, $R_1$ or $R_2$ is preferably H and the remaining $R_1$ or $R_2$ is preferably linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, even more preferably linear $C_1$-$C_3$-alkyl, and most preferably $C_1$- or $C_2$-alkyl, e.g. $C_2$-alkyl.

Preferably, $R_1$ and $R_2$ are the same.

The alkyl aryl ketone of the general formula I further comprises residues $R_3$, $R_4$, $R_5$, $R_6$ and $R_7$. It is appreciated that $R_3$, $R_4$, $R_5$, $R_6$ and $R_7$ can be the same or different. Furthermore, $R_3$, $R_4$, $R_5$, $R_6$ and $R_7$ are the same or different and are independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_6$-$C_{14}$-aryl, $C_3$-$C_8$-cycloalkoxy, $C_7$-$C_{15}$-arylalkoxy, $C_9$-$C_{15}$-alkenylarylalkoxy, $N(R_8)_2$ or $SR_8$ with $R_8$ being selected from linear or branched $C_1$-$C_8$-alkyl, linear or branched $C_2$-$C_8$-alkenyl, $C_6$-$C_{14}$-aryl, $C_1$-$C_8$-alkoxy, $C_2$-$C_8$-alkenyloxy, $C_3$-$C_8$-cycloalkyl, $C_3$-$C_8$-cycloalkoxy, $C_7$-$C_{15}$-arylalkoxy, $C_9$-$C_{15}$-alkenylarylalkoxy, or $R_8$ form a $C_3$-$C_9$-alicyclic system together with the connecting N atom, or $R_8$ form a $C_3$-$C_9$-alicyclic system together with the connecting N atom, optionally one or more carbon atoms are replaced with O, or two adjacent R form an aromatic system together with the benzene ring of formula I.

The term "$C_1$-$C_8$-alkoxy" in the meaning of the present invention means that the alkoxy moiety has a linear or branched chain alkyl having 1 to 8 carbon atoms, and includes, for example, methoxy, ethoxy, propoxy, isopropoxy, butoxy, isobutoxy, tertiary butoxy, pentyloxy, hexyloxy, heptyloxy and octyloxy.

The term "$C_2$-$C_8$-alkenyloxy" in the meaning of the present invention means that the alkenyloxy moiety has a linear or branched chain alkenyl having 2 to 8 carbon atoms, and includes, for example, ethenyloxy, propenyloxy, butenyloxy, triisobutenyloxy, pentenyloxy, hexenyloxy, heptenyloxy and octenyloxy.

The term "$C_3$-$C_8$-cycloalkoxy" in the meaning of the present invention means that the cycloalkoxy moiety has a cyclic alkyl having 3 to 8 carbon atoms, and includes, for example, cyclopropyloxy, cyclobutyloxy, cyclopentyloxy, cyclohexyloxy, and cycloheptyloxy.

The term "$C_7$-$C_{15}$-arylalkoxy" in the meaning of the present invention means that the alkoxy moiety has a linear or branched chain alkyl having 1 to 4 carbon atoms, preferably 1 or 2 carbon atoms, which is connected to $C_6$-$C_{14}$-aryl.

The term "$C_7$-$C_{15}$-arylalkyl" in the meaning of the present invention means that the alkyl moiety is a linear or branched chain alkyl having 1 to 4 carbon atoms, preferably 1 or 2 carbon atoms, which is connected to $C_6$-$C_{14}$-aryl.

The term "$C_9$-$C_{15}$-alkenylarylalkoxy" in the meaning of the present invention means that the alkoxy moiety has a linear or branched chain alkyl having 1 to 4 carbon atoms, preferably 1 or 2 carbon atoms, which is connected to $C_6$-$C_{14}$-aryl, preferably $C_6$-aryl, which is further connected to linear or branched $C_2$-$C_8$-alkenyl, preferably $C_2$-alkenyl. Preferably, the alkoxy and alkenyl moieties are connected in para-position of the aryl moiety.

In one embodiment, $R_3$, $R_4$, $R_5$, $R_6$ and $R_7$ are the same. In this embodiment, $R_3$, $R_4$, $R_5$, $R_6$ and $R_7$ are the same and are selected from H and linear or branched $C_1$-$C_8$-alkyl, e.g. linear $C_1$-$C_8$-alkyl. For example, $R_3$, $R_4$, $R_5$, $R_6$ and $R_7$ are the same and are linear or branched $C_1$-$C_6$-alkyl, e.g. linear $C_1$-$C_6$-alkyl, preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl. It is especially preferred that $R_3$, $R_4$, $R_5$, $R_6$ and $R_7$ are the same and are H.

Alternatively, $R_3$, $R_4$, $R_5$, $R_6$ and $R_7$ are different. In this embodiment, $R_3$, $R_4$, $R_5$, $R_6$ and $R_7$ are different and at least one of them is selected from linear or branched $C_1$-$C_8$-alkyl, linear or branched $C_2$-$C_8$-alkenyl, $C_1$-$C_8$-alkoxy, $C_2$-$C_8$-alkenyloxy, $C_9$-$C_{15}$-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom.

The term "at least one" in the meaning of the present invention means that one or more of $R_3$, $R_4$, $R_5$, $R_6$ and $R_7$ is selected from linear or branched $C_1$-$C_8$-alkyl, linear or branched $C_2$-$C_8$-alkenyl, $C_1$-$C_8$-alkoxy, $C_2$-$C_8$-alkenyloxy, $C_9$-$C_{15}$-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom.

For example, one or two or three of $R_3$, $R_4$, $R_5$, $R_6$ and $R_7$ is/are selected from linear or branched $C_1$-$C_8$-alkyl, linear or branched $C_2$-$C_8$-alkenyl, $C_1$-$C_8$-alkoxy, $C_2$-$C_8$-alkenyloxy, $C_9$-$C_{15}$-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom. For example, one or two of $R_3$, $R_4$, $R_5$, $R_6$ and $R_7$ is/are selected from linear or branched $C_1$-$C_8$-alkyl, linear or branched $C_2$-$C_8$-alkenyl, $C_1$-$C_8$-alkoxy, $C_2$-$C_8$-alkenyloxy, $C_9$-$C_{15}$-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom.

Preferably, one of $R_3$, $R_4$, $R_5$, $R_6$ and $R_7$ is selected from linear or branched $C_1$-$C_8$-alkyl, linear or branched $C_2$-$C_8$-alkenyl, $C_1$-$C_8$-alkoxy, $C_2$-$C_8$-alkenyloxy, $C_9$-$C_{15}$-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom.

If $R_3$, $R_4$, $R_5$, $R_6$ and $R_7$ are different and at least one of them is selected from linear or branched $C_1$-$C_8$-alkyl, linear or branched $C_2$-$C_8$-alkenyl, $C_1$-$C_8$-alkoxy, $C_2$-$C_8$-alkenyloxy, $C_9$-$C_{15}$-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom, it is preferred that the remaining ones are selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl, e.g. $C_1$- or $C_2$-alkyl. For example, $R_3$, $R_4$, $R_5$, $R_6$ and $R_7$ are different and at least one of them is selected from linear or branched $C_1$-$C_8$-alkyl, linear or branched $C_2$-$C_8$-alkenyl, $C_1$-$C_8$-alkoxy, $C_2$-$C_8$-alkenyloxy, $C_9$-$C_{15}$-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom and the remaining ones are H.

In one embodiment, $R_3$, $R_4$, $R_5$, $R_6$ and $R_7$ are different and one of them is selected from linear or branched $C_1$-$C_8$-alkyl, linear or branched $C_2$-$C_8$-alkenyl, $C_1$-$C_8$-alkoxy, $C_2$-$C_8$-alkenyloxy, $C_9$-$C_{15}$-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom.

For example, $R_3$, $R_4$, $R_5$, $R_6$ and $R_7$ are different and one of them is linear or branched $C_2$-$C_8$-alkenyl, e.g. linear $C_2$-$C_8$-alkenyl; preferably linear or branched $C_2$-$C_6$-alkenyl, e.g. linear $C_2$-$C_6$-alkenyl; and most preferably $C_2$-$C_3$-alkenyl, e.g. $C_2$- or $C_3$-alkenyl; and the remaining ones are H.

Alternatively, $R_3$, $R_4$, $R_5$, $R_6$ and $R_7$ are different and one of them is $C_2$-$C_8$-alkenyloxy, preferably $C_2$-$C_6$-alkenyloxy and most preferably $C_3$-$C_5$-alkenyloxy, e.g. $C_3$- or $C_4$-alkenyloxy, especially $C_3$-alkenyloxy; and the remaining ones are H.

In one embodiment, $R_3$, $R_4$, $R_5$, $R_6$ and $R_7$ are different and one of them is $C_2$-$C_8$-alkenyloxy, preferably $C_2$-$C_6$-alkenyloxy and most preferably $C_3$-$C_5$-alkenyloxy, e.g. $C_3$- or $C_4$-alkenyloxy, especially $C_3$-alkenyloxy; and the remaining ones are independently selected from H and linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl.

For example, $R_3$, $R_4$, $R_5$, $R_6$ and $R_7$ are different and one of them is $C_2$-$C_8$-alkenyloxy, preferably $C_2$-$C_6$-alkenyloxy and most preferably $C_3$-$C_5$-alkenyloxy, e.g. $C_3$- or $C_4$-alkenyloxy, especially $C_3$-alkenyloxy; and two of the remaining ones are H and two of the remaining ones are linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl.

Alternatively, $R_3$, $R_4$, $R_5$, $R_6$ and $R_7$ are different and one of them is $C_9$-$C_{15}$-alkenylarylalkoxy, preferably $C_9$-$C_{12}$-alkenylarylalkoxy and most preferably $C_9$-$C_{10}$-alkenylarylalkoxy; and the remaining ones are H.

Alternatively, $R_3$, $R_4$, $R_5$, $R_6$ and $R_7$ are different and one of them is $SR_8$ with $R_8$ being selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; and the remaining ones are H.

Alternatively, $R_3$, $R_4$, $R_5$, $R_6$ and $R_7$ are different and one of them is $N(R_8)_2$ with $R_8$ forming a $C_3$-$C_9$-alicyclic system, preferably a $C_3$-$C_7$-alicyclic system, more preferably a $C_4$-$C_6$-alicyclic system and most preferably a $C_5$- or $C_6$-alicyclic system, together with the connecting N atom; and the remaining ones are H. Optionally one or more carbon atoms are replaced with O. Preferably, $R_3$, $R_4$, $R_5$, $R_6$ and $R_7$ are different and one of them is $N(R_8)_2$ with $R_8$ forming a $C_3$-$C_9$-alicyclic system, preferably a $C_3$-$C_7$-alicyclic system, more preferably a $C_4$-$C_6$-alicyclic system and most preferably a $C_5$- or $C_6$-alicyclic system, together with the connecting N atom, wherein one or more, preferably one, carbon atoms are replaced with O; and the remaining ones are H.

If $R_3$, $R_4$, $R_5$, $R_6$ and $R_7$ are different and one of them is selected from linear or branched $C_1$-$C_8$-alkyl, linear or branched $C_2$-$C_8$-alkenyl, $C_1$-$C_8$-alkoxy, $C_2$-$C_8$-alkenyloxy, $C_9$-$C_{15}$-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom, it is preferred that $R_5$ is selected from linear or branched $C_1$-$C_8$-alkyl, linear or branched $C_2$-$C_8$-alkenyl, $C_1$-$C_8$-alkoxy, $C_2$-$C_8$-alkenyloxy, $C_9$-$C_{15}$-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom.

Thus, if $R_3$, $R_4$, $R_5$, $R_6$ and $R_7$ are different and one of them is selected from linear or branched $C_1$-$C_8$-alkyl, linear or branched $C_2$-$C_8$-alkenyl, $C_1$-$C_8$-alkoxy, $C_2$-$C_8$-alkenyloxy, $C_9$-$C_{15}$-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom, it is preferred that this group is in para-position to the keto group.

In an alternative embodiment, $R_3$, $R_4$, $R_5$, $R_6$ and $R_7$ are different and two or three of them are linear or branched $C_2$-$C_8$-alkenyl, e.g. linear $C_2$-$C_8$-alkenyl, preferably linear or branched $C_2$-$C_6$-alkenyl, e.g. linear $C_2$-$C_6$-alkenyl, and most preferably $C_2$-$C_3$-alkenyl; $C_1$-$C_8$-alkoxy, preferably $C_1$-$C_6$-alkoxy and most preferably $C_1$-$C_3$-alkoxy; $C_2$-$C_8$-alkenyloxy, preferably $C_2$-$C_6$-alkenyloxy and most preferably $C_3$-$C_5$-alkenyloxy; and $C_9$-$C_{15}$-alkenylarylalkoxy, preferably $C_9$-$C_{12}$-alkenylarylalkoxy and most preferably $C_9$-$C_{10}$-alkenylarylalkoxy, and the remaining ones are independently selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl, e.g. $C_1$- or $C_2$-alkyl, especially $C_1$-alkyl.

For example, $R_3$, $R_4$, $R_5$, $R_6$ and $R_7$ are different and two of them are linear or branched $C_2$-$C_8$-alkenyl, e.g. linear $C_2$-$C_8$-alkenyl, preferably linear or branched $C_2$-$C_6$-alkenyl, e.g. linear $C_2$-$C_6$-alkenyl, and most preferably $C_2$-$C_3$-alkenyl; $C_1$-$C_8$-alkoxy, preferably $C_1$-$C_6$-alkyloxy and most preferably $C_1$-$C_3$-alkyloxy; $C_2$-$C_8$-alkenyloxy, preferably $C_2$-$C_6$-alkenyloxy and most preferably $C_3$-$C_5$-alkenyloxy; and $C_9$-$C_{15}$-alkenylarylalkoxy, preferably $C_9$-$C_{12}$-alkenylarylalkoxy and most preferably $C_9$-$C_{10}$-alkenylarylalkoxy, and the remaining ones are independently selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl, e.g. $C_1$- or $C_2$-alkyl, especially $C_1$-alkyl. Preferably, $R_3$, $R_4$, $R_5$, $R_6$ and $R_7$ are different and two of them are $C_2$-$C_8$-alkenyloxy, preferably $C_2$-$C_6$-alkenyloxy and most preferably $C_3$-$C_5$-alkenyloxy; and the remaining ones are independently selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl, e.g. $C_1$- or $C_2$-alkyl, especially $C_1$-alkyl, preferably the remaining ones are H.

Alternatively, $R_3$, $R_4$, $R_5$, $R_6$ and $R_7$ are different and two of them are $C_1$-$C_8$-alkoxy, preferably $C_1$-$C_6$-alkoxy and most preferably $C_1$-$C_3$-alkoxy; and the remaining ones are independently selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl, e.g. $C_1$- or $C_2$-alkyl, especially $C_1$-alkyl, preferably the remaining ones are H.

In one embodiment, $R_3$, $R_4$, $R_5$, $R_6$ and $R_7$ are different and three of them are $C_9$-$C_{15}$-alkenylarylalkoxy, preferably $C_9$-$C_{12}$-alkenylarylalkoxy and most preferably $C_9$-$C_{10}$-alkenylarylalkoxy, and the remaining ones are independently selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl, e.g. $C_1$- or $C_2$-alkyl, especially $C_1$-alkyl, preferably the remaining ones are H.

If two or three of $R_3$, $R_4$, $R_5$, $R_6$ and $R_7$ are linear or branched $C_2$-$C_8$-alkenyl, e.g. linear $C_2$-$C_8$-alkenyl, preferably linear or branched $C_2$-$C_6$-alkenyl, e.g. linear $C_2$-$C_6$-alkenyl, and most preferably $C_2$-$C_3$-alkenyl; $C_1$-$C_8$-alkoxy, preferably $C_1$-$C_6$-alkyloxy and most preferably $C_1$-$C_3$-alkyloxy; $C_2$-$C_8$-alkenyloxy, preferably $C_2$-$C_6$-alkenyloxy and most preferably $C_3$-$C_5$-alkenyloxy; and $C_9$-$C_{15}$-alkenylarylalkoxy, preferably $C_9$-$C_{12}$-alkenylarylalkoxy and most preferably $C_9$-$C_{10}$-alkenylarylalkoxy, it is appreciated that preferably $R_4$ and/or $R_5$ and/or $R_6$ are linear or branched $C_2$-$C_8$-alkenyl, e.g. linear $C_2$-$C_8$-alkenyl, preferably linear or branched $C_2$-$C_6$-alkenyl, e.g. linear $C_2$-$C_6$-alkenyl, and most preferably $C_2$-$C_3$-alkenyl; $C_1$-$C_8$-alkoxy, preferably $C_1$-$C_6$-alkyloxy and most preferably $C_1$-$C_3$-alkyloxy; $C_2$-$C_8$-alkenyloxy, preferably $C_2$-$C_6$-alkenyloxy and most preferably $C_3$-$C_5$-alkenyloxy; and $C_9$-$C_{15}$-alkenylarylalkoxy, preferably $C_9$-$C_{12}$-alkenylarylalkoxy and most preferably $C_9$-$C_{10}$-alkenylarylalkoxy.

In one embodiment, $R_3$ and $R_4$ or $R_4$ and $R_5$ form an aromatic system together with the benzene ring of general formula I, preferably a bicyclic, tricyclic or tetracyclic aromatic system, more preferably an aromatic system selected from a naphthyl, anthracenyl and phenanthrenyl system. The aromatic system is preferably a bicyclic aromatic system, most preferably naphthyl.

For example, $R_4$ and $R_5$ form an aromatic system together with the benzene ring of general formula I, preferably a bicyclic aromatic system, most preferably naphthyl; and the remaining ones are independently selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl, e.g. $C_1$- or $C_2$-alkyl, especially $C_1$-alkyl, preferably H.

It is appreciated that one of the remaining R may be linear or branched $C_2$-$C_8$-alkenyl, preferably $C_2$-$C_6$-alkenyl and most preferably $C_2$-$C_3$-alkenyl; $C_2$-$C_8$-alkenyloxy, preferably $C_2$-$C_6$-alkenyloxy and most preferably $C_3$-$C_5$-alkenyloxy; and $C_9$-$C_{15}$-alkenylarylalkoxy, preferably $C_9$-$C_{12}$-alkenylarylalkoxy and most preferably $C_9$-$C_{10}$-alkenylarylalkoxy; and the remaining ones may be independently selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl, e.g. $C_1$- or $C_2$-alkyl, especially $C_1$-alkyl, preferably H.

In one embodiment, $R_4$ and $R_5$ form an aromatic system together with the benzene ring of general formula I, preferably a bicyclic aromatic system, most preferably naphthyl, and $R_3$ is linear or branched $C_2$-$C_8$-alkenyl, preferably $C_2$-$C_6$-alkenyl and most preferably $C_2$-$C_3$-alkenyl; $C_2$-$C_8$-alkenyloxy, preferably $C_2$-$C_6$-alkenyloxy and most preferably $C_3$-$C_5$-alkenyloxy; and $C_9$-$C_{15}$-alkenylarylalkoxy, preferably $C_9$-$C_{12}$-alkenylarylalkoxy and most preferably $C_9$-$C_{10}$-alkenylarylalkoxy; and the remaining ones are independently selected from H and linear or branched $C_1$-$C_8$-alkyl, preferably linear or branched $C_1$-$C_6$-alkyl, more preferably linear or branched $C_1$-$C_4$-alkyl and most preferably linear $C_1$-$C_3$-alkyl, preferably H. For example, $R_4$ and $R_5$ form an aromatic system together with the benzene ring of general formula I, preferably a bicyclic aromatic system, most preferably naphthyl, and $R_3$ is $C_9$-$C_{15}$-alkenylarylalkoxy, preferably $C_9$-$C_{12}$-alkenylarylalkoxy and most preferably $C_9$-$C_{10}$-alkenylarylalkoxy; and the remaining ones are H.

An especially preferred alkyl aryl ketone of the general formula I is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; and $R_3$, $R_4$, $R_5$, $R_6$ and $R_7$ are the same and are H.

For example, the alkyl aryl ketone of the general formula I is a ketone, wherein $R_1$ and $R_2$ are the same and are $C_1$-alkyl; and $R_3$, $R_4$, $R_5$, $R_6$ and $R_7$ are the same and are H.

Alternatively, the alkyl aryl ketone of the general formula I is a ketone, wherein $R_1$ and $R_2$ form $C_3$-$C_{12}$-cycloalkyl, preferably $C_4$-$C_{10}$-cycloalkyl, more preferably $C_4$-$C_8$-cycloalkyl, even more preferably $C_4$-$C_6$-cycloalkyl, and most preferably $C_5$- or $C_6$-cycloalkyl, e.g. $C_6$-cycloalkyl, together with the connecting C atom; and $R_4$, $R_5$, $R_6$ and $R_7$ are the same and are H.

Alternatively, the alkyl aryl ketone of the general formula I is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; and $R_4$, $R_5$, $R_6$ and $R_7$ are the same and are H.

Alternatively, the alkyl aryl ketone of the general formula I is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_4$, $R_5$, $R_6$ and $R_7$ are different and one of them, preferably $R_5$, is linear or branched $C_2$-$C_8$-alkenyl, preferably linear or branched $C_2$-$C_6$-alkenyl and most preferably $C_2$-$C_3$-alkenyl, e.g. $C_2$-alkenyl; and the remaining ones are H.

For example, the alkyl aryl ketone of the general formula I is a ketone, wherein $R_1$ and $R_2$ are the same and are $C_1$-alkyl; $R_4$, $R_5$, $R_6$ and $R_7$ are different and one of them, preferably $R_5$, is linear or branched $C_2$-$C_8$-alkenyl, preferably linear or branched $C_2$-$C_6$-alkenyl and most preferably $C_2$-$C_3$-alkenyl, e.g. $C_2$-alkenyl; and the remaining ones are H.

Alternatively, the alkyl aryl ketone of the general formula I is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_4$, $R_5$, $R_6$ and $R_7$ are different and one of them, preferably $R_5$, is linear or branched $C_2$-$C_8$-alkenyl, preferably linear or branched $C_2$-$C_6$-alkenyl and most preferably $C_2$-$C_3$-alkenyl, e.g. $C_2$-alkenyl; and the remaining ones are H.

For example, the alkyl aryl ketone of the general formula I is a ketone, wherein $R_1$ and $R_2$ are the same and are $C_1$-alkyl; $R_4$, $R_5$, $R_6$ and $R_7$ are different and one of them, preferably $R_5$, is linear or branched $C_2$-$C_8$-alkenyl, preferably linear or branched $C_2$-$C_6$-alkenyl and most preferably $C_2$-$C_3$-alkenyl, e.g. $C_2$-alkenyl; and the remaining ones are H.

Alternatively, the alkyl aryl ketone of the general formula I is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_4$, $R_5$, $R_6$ and $R_7$ are different and one of them, preferably $R_5$, is $SR_8$ with $R_8$ being selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear or branched $C_1$-$C_3$-alkyl, e.g. linear $C_1$- or $C_3$-alkyl, especially $C_1$-alkyl; and the remaining ones are H.

For example, the alkyl aryl ketone of the general formula I is a ketone, wherein $R_1$ and $R_2$ are the same and are $C_1$-alkyl; $R_4$, $R_5$, $R_6$ and $R_7$ are different and one of them, preferably $R_5$, is $SR_8$ with $R_8$ being selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; and the remaining ones are H.

Alternatively, the alkyl aryl ketone of the general formula I is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_4$, $R_5$, $R_6$ and $R_7$ are different and one of them, preferably $R_5$, is $SR_8$ with $R_8$ being selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; and the remaining ones are H.

For example, the alkyl aryl ketone of the general formula I is a ketone, wherein $R_1$ and $R_2$ are the same and are $C_1$-alkyl; $R_4$, $R_5$, $R_6$ and $R_7$ are different and one of them, preferably $R_5$, is $SR_8$ with $R_8$ being selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; and the remaining ones are H.

Alternatively, the alkyl aryl ketone of the general formula I is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_3$, $R_4$, $R_5$, $R_6$ and $R_7$ are different and one of them is $C_2$-$C_8$-alkenyloxy, preferably $C_2$-$C_6$-alkenyloxy and most preferably $C_3$-$C_5$-alkenyloxy, e.g. $C_3$- or $C_4$-alkenyloxy, especially $C_3$-alkenyloxy; and two of the remaining ones are H and two of the remaining ones are linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl.

For example, the alkyl aryl ketone of the general formula I is a ketone, wherein $R_1$ and $R_2$ are the same and are $C_1$-alkyl; $R_3$, $R_4$, $R_5$, $R_6$ and $R_7$ are different and one of them, preferably $R_5$, is $C_2$-$C_8$-alkenyloxy, preferably $C_2$-$C_6$-alkenyloxy and most preferably $C_3$-$C_5$-alkenyloxy, e.g. $C_3$- or $C_4$-alkenyloxy, especially $C_3$-alkenyloxy; and two of the remaining ones, preferably $R_3$ and $R_7$, are H and two of the remaining ones, preferably $R_4$ and $R_6$, are linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl.

Alternatively, the alkyl aryl ketone of the general formula I is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_3$, $R_4$, $R_5$, $R_6$ and $R_7$ are different and three of them, preferably $R_3$ and $R_4$ and $R_5$, are $C_9$-$C_{15}$-alkenylarylalkoxy, preferably $C_9$-$C_{12}$-alkenylarylalkoxy and most preferably $C_9$-$C_{10}$-alkenylarylalkoxy, and the remaining ones, preferably $R_6$ and $R_7$ are H.

For example, the alkyl aryl ketone of the general formula I is a ketone, wherein $R_1$ and $R_2$ are the same and are $C_1$-alkyl; $R_3$, $R_4$, $R_5$, $R_6$ and $R_7$ are different and three of them, preferably $R_3$ and $R_4$ and $R_5$, are $C_9$-$C_{15}$-alkenylarylalkoxy, preferably $C_9$-$C_{12}$-alkenylarylalkoxy and most preferably $C_9$-$C_{10}$-alkenylarylalkoxy, and the remaining ones, preferably $R_6$ and $R_7$ are H.

Alternatively, the alkyl aryl ketone of the general formula I is a ketone, wherein $R_1$ and $R_2$ are different and are selected from H and linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_3$, $R_4$, $R_5$, $R_6$ and $R_7$ are different and two of them, preferably $R_4$ and $R_5$, are $C_1$-$C_8$-alkoxy, preferably $C_1$-$C_6$- alkoxy and most preferably $C_1$-$C_3$-alkoxy, especially $C_1$-alkoxy; and the remaining ones, preferably $R_3$, $R_6$ and $R_7$, are H.

For example, the alkyl aryl ketone of the general formula I of the general formula I is a ketone, wherein $R_1$ and $R_2$ are different and are H and $C_2$-alkyl; $R_3$, $R_4$, $R_5$, $R_6$ and $R_7$ are different and two of them, preferably $R_4$ and $R_5$, are $C_1$-$C_8$-alkoxy, preferably $C_1$-$C_6$-alkoxy and most preferably $C_1$-$C_3$-alkoxy, especially $C_1$-alkoxy; and the remaining ones, preferably $R_3$, $R_6$ and $R_7$, are H.

Alternatively, the alkyl aryl ketone of the general formula I is a ketone, wherein $R_1$ and $R_2$ are different and are selected from H and linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_3$, $R_4$, $R_5$, $R_6$ and $R_7$ are different and one of them, preferably $R_5$, is $N(R_8)_2$ with $R_8$ forming a $C_3$-$C_9$-alicyclic system, preferably a $C_3$-$C_7$-alicyclic system, more preferably a $C_4$-$C_6$-alicyclic system and most preferably a $C_5$- or $C_6$-alicyclic system, together with the connecting N atom, wherein one or more, preferably one, carbon atoms are replaced with O; and the remaining ones, preferably $R_3$, $R_4$, $R_6$ and $R_7$, are H.

For example, the alkyl aryl ketone of the general formula I is a ketone, wherein $R_1$ and $R_2$ are different and are H and $C_2$-alkyl; $R_3$, $R_4$, $R_5$, $R_6$ and $R_7$ are different and one of them, preferably $R_5$, is $N(R_8)_2$ with $R_8$ forming a $C_3$-$C_9$-alicyclic system, preferably a $C_3$-$C_7$-alicyclic system, more preferably a $C_4$-$C_6$-alicyclic system and most preferably a $C_5$- or $C_6$-alicyclic system, together with the connecting N atom, wherein one or more, preferably one, carbon atoms are replaced with O; and the remaining ones, preferably $R_3$, $R_4$, $R_6$ and $R_7$, are H.

Alternatively, the alkyl aryl ketone of the general formula I is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_4$ and $R_5$ form an aromatic system together with the benzene ring of general formula I, preferably a bicyclic aromatic system, most preferably naphthyl; and the remaining ones are independently selected from H and linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl, preferably H.

For example, the alkyl aryl ketone of the general formula I is a ketone, wherein $R_1$ and $R_2$ are the same and are $C_1$-alkyl; $R_4$ and $R_5$ form an aromatic system together with the benzene ring of general formula I, preferably a bicyclic aromatic system, most preferably naphthyl; and the remaining ones are H.

Alternatively, the alkyl aryl ketone of the general formula I is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_4$ and $R_5$ form an aromatic system together with the benzene ring of general formula I, preferably a bicyclic aromatic system, most preferably naphthyl; and one of the remaining R, preferably $R_3$, is linear or branched $C_2$-$C_8$-alkenyl, preferably $C_2$-$C_6$-alkenyl and most preferably $C_2$-$C_3$-alkenyl; $C_2$-$C_8$-alkenyloxy, preferably $C_2$-$C_6$-alkenyloxy and most preferably $C_3$-$C_5$-alkenyloxy; and $C_9$-$C_{15}$-alkenylarylalkoxy, preferably $C_9$-$C_{12}$-alkenylarylalkoxy and most preferably $C_9$-$C_{10}$-alkenylarylalkoxy and the remaining ones are H.

For example, the alkyl aryl ketone of the general formula I is a ketone, wherein $R_1$ and $R_2$ are the same and are $C_1$-alkyl; $R_4$ and $R_5$ form an aromatic system together with the benzene ring of general formula I, preferably a bicyclic aromatic system, most preferably naphthyl; and one of the remaining R, preferably $R_3$, is $C_9$-$C_{15}$-alkenylarylalkoxy, preferably $C_9$-$C_{12}$-alkenylarylalkoxy and most preferably $C_9$-$C_{10}$-alkenylarylalkoxy and the remaining ones are H.

It is appreciated that the alkyl aryl ketone of the general formula I is reacted with an at least partially halogenated $C_2$-$C_8$-alkane and/or $C_2$-$C_8$-alkene, and a base selected from alkali metal $C_1$-$C_8$-alkoxide, earth alkali metal $C_1$-$C_8$-alkoxide and mixtures thereof, obtaining thereby the corresponding aryl oxirane or α-functionalized alkyl aryl ketal.

It is preferred that the at least partially halogenated $C_2$-$C_8$-alkane and/or $C_2$-$C_8$-alkene is an at least partially halogenated $C_2$-$C_6$-alkane and/or $C_2$-$C_6$-alkene, more preferably an at least partially halogenated $C_2$-$C_4$-alkane and/or $C_2$-$C_4$-alkene. For example, the at least partially halogenated $C_2$-$C_8$-alkane and/or $C_2$-$C_8$-alkene is an at least partially halogenated $C_2$- or $C_3$-alkane and/or $C_2$- or $C_3$-alkene, e.g. an at least partially halogenated $C_2$-alkane and/or $C_2$-alkene.

The at least partially halogenated $C_2$-$C_8$-alkane and/or $C_2$-$C_8$-alkene may be at least partially chlorinated and/or brominated. For example, the at least partially halogenated $C_2$-$C_8$-alkane and/or $C_2$-$C_8$-alkene is at least partially chlorinated or brominated. Alternatively, the at least partially halogenated $C_2$-$C_8$-alkane and/or $C_2$-$C_8$-alkene is at least partially chlorinated and brominated, and thus is a mixed halogenated $C_2$-$C_8$-alkane and/or $C_2$-$C_8$-alkene.

Preferably, the at least partially halogenated $C_2$-$C_8$-alkane and/or $C_2$-$C_8$-alkene is at least partially chlorinated.

In one embodiment, the at least partially halogenated $C_2$-$C_8$-alkane and/or $C_2$-$C_8$-alkene is fully halogenated. Preferably, the at least partially halogenated $C_2$-$C_8$-alkane and/or $C_2$-$C_8$-alkene is a fully halogenated $C_2$-$C_6$-alkane and/or $C_2$-$C_6$-alkene, more preferably a fully halogenated $C_2$-$C_4$-alkane and/or $C_2$-$C_4$-alkene. For example, the at least partially halogenated $C_2$-$C_8$-alkane and/or $C_2$-$C_8$-alkene is a fully halogenated $C_2$- or $C_3$-alkane and/or $C_2$- or $C_3$-alkene.

For example, the at least partially halogenated $C_2$-$C_8$-alkane and/or $C_2$-$C_8$-alkene may be fully chlorinated and/or brominated. For example, the at least partially halogenated $C_2$-$C_8$-alkane and/or $C_2$-$C_8$-alkene is fully chlorinated or brominated. Alternatively, the at least partially halogenated $C_2$-$C_8$-alkane and/or $C_2$-$C_8$-alkene is fully chlorinated and brominated, and thus is a mixed halogenated $C_2$-$C_8$-alkane and/or $C_2$-$C_8$-alkene.

Preferably, the at least partially halogenated $C_2$-$C_8$-alkane and/or $C_2$-$C_8$-alkene is fully chlorinated.

In one embodiment, the at least partially halogenated $C_2$-$C_8$-alkane and/or $C_2$-$C_8$-alkene is selected from hexachloroethane, tetrachoroethylene, pentachloropropane, hexabromoethane, tetrabromoethylene, pentabromopropane and mixtures thereof. Preferably, the at least partially halogenated $C_2$-$C_8$-alkane and/or $C_2$-$C_8$-alkene is hexachloroethane, tetrachoroethylene and mixtures thereof. For example, the at least partially halogenated $C_2$-$C_8$-alkane and/or $C_2$-$C_8$-alkene is hexachloroethane or tetrachoroethylene.

In one embodiment, the at least partially halogenated $C_2$-$C_8$-alkane and/or $C_2$-$C_8$-alkene is hexachloroethane.

Another requirement of the process is the addition of a base. It is a requirement of the present invention that the base is selected from the group comprising alkali metal $C_1$-$C_8$-alkoxide, earth alkali metal $C_1$-$C_8$-alkoxide and mixtures thereof.

In one embodiment, the base is selected from the group comprising sodium $C_1$-$C_6$-alkoxide, preferably sodium $C_1$-$C_4$-alkoxide and most preferably sodium $C_1$-$C_2$-alkoxide; lithium $C_1$-$C_6$-alkoxide, preferably lithium $C_1$-$C_4$-alkoxide and most preferably lithium $C_1$-$C_2$-alkoxide; potassium $C_1$-$C_6$-alkoxide, preferably potassium $C_1$-$C_4$-alkoxide and most preferably potassium $C_1$-$C_2$-alkoxide; and mixtures thereof. Preferably, the base is sodium $C_1$-$C_6$-alkoxide, preferably sodium $C_1$-$C_4$-alkoxide and most preferably sodium $C_1$-$C_2$-alkoxide. Most preferably, the base is sodium $C_1$-alkoxide.

The base can be added as such into the process. Alternatively, the base is in form of an aqueous solution or the base is provided in an organic solvent, preferably the organic solvent is selected from the group comprising methanol, ethanol, n-propanol, tert.-butanol, dichloromethane, tetrachloroethylene, tetrahydrofuran, ethyl acetate, acetone, N,N-dimethylformamide, dimethyl sulfoxide and mixtures thereof. Preferably, the base is provided in an organic solvent, preferably the organic solvent is methanol.

The process of the present invention can be carried out over a wide temperature range. For example, the process is carried out at a temperature in the range from 0 to 120° C., preferably in the range from 12 to 80° C., more preferably in the range from to 50° C., and most preferably in the range from 15 to 30° C.

Preferably, the process is carried out at room temperature, i.e. at a temperature of about 21° C. (±2° C.).

In one embodiment, it is preferred that the process is carried out at elevated temperature. That is to say, the process is carried out at a temperature above room temperature, preferably in the range from 30 to 120° C., more preferably in the range from 40 to 100° C., and most preferably in the range from 40 to 90° C.

It is further appreciated that the process can be carried out in an organic solvent. Preferably the organic solvent is selected from the group comprising methanol, ethanol, n-propanol, tert.-butanol, dichloromethane, tetrachloroethylene, tetrahydrofuran, ethyl acetate, acetone, N,N-dimethylformamide, dimethyl sulfoxide, dioxane such as 1,3-dioxane or 1,4-dioxane, 1,2-dimethoxyethane, diethyleneglycol dimethyl ether, triethyleneglycol dimethyl ether and mixtures thereof.

If the base is provided in an organic solvent, the organic solvent is preferably the same as used in the process. Thus, the organic solvent is preferably methanol.

The reaction and contacting are carried out by mixing the components, i.e. the alkyl aryl ketone of the general formula I, the at least partially halogenated $C_2$-$C_8$-alkane and/or $C_2$-$C_8$-alkene, and the base selected from alkali metal $C_1$-$C_8$-alkoxide, earth alkali metal $C_1$-$C_8$-alkoxide and mixtures thereof. The skilled man will adapt the mixing conditions (such as the configuration of mixing tools and mixing speed) according to his process equipment.

It has been found that the sequence of addition of the reagents is unimportant for the success of the reaction. Thus, the alkyl aryl ketone of the general formula I, the base selected from alkali metal $C_1$-$C_8$-alkoxide, earth alkali metal $C_1$-$C_8$-alkoxide and mixtures thereof, the at least partially halogenated $C_2$-$C_8$-alkane and/or $C_2$-$C_8$-alkene and, if present, the organic solvent, can be contacted in any order.

Preferably, the alkyl aryl ketone of the general formula I, the base selected from alkali metal $C_1$-$C_8$-alkoxide, earth alkali metal $C_1$-$C_8$-alkoxide and mixtures thereof, and, if present, the organic solvent are contacted first and the at least partially halogenated $C_2$-$C_8$-alkane and/or $C_2$-$C_8$-alkene is metered in.

It is appreciated that the process for reacting the alkyl aryl ketone of the general formula I, with the at least partially halogenated $C_2$-$C_8$-alkane and/or $C_2$-$C_8$-alkene, and a base selected from alkali metal $C_1$-$C_8$-alkoxide, earth alkali metal $C_1$-$C_8$-alkoxide and mixtures thereof, results in the corresponding aryl oxirane or α-functionalized alkyl aryl ketal. The obtained aryl oxirane is preferably of the following general formula Ia.

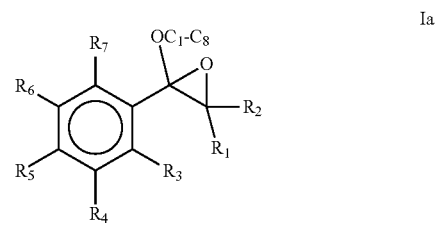

Ia

With regard to the definition of $R_1$, $R_2$, $R_3$, $R_4$, $R_5$, $R_6$, and $R_7$ and preferred embodiments thereof, reference is made to the statements provided above when discussing the technical details of the process and the alkyl aryl ketone of the general formula I used as starting material in the process of the present invention.

The obtained α-functionalized alkyl aryl ketal is preferably of the following general formula Ib.

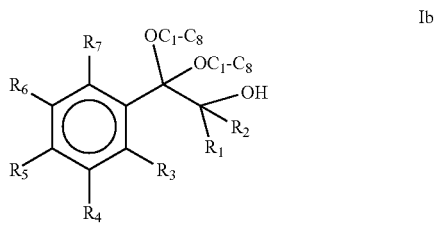

Ib

With regard to the definition of $R_1$, $R_2$, $R_3$, $R_4$, $R_5$, $R_6$, and $R_7$ and preferred embodiments thereof, reference is made to the statements provided above when discussing the technical details of the process and the alkyl aryl ketone of the general formula I used as starting material in the process of the present invention.

The process of the present invention may comprise further steps for isolating and/or purifying the obtained aryl oxirane or α-functionalized alkyl aryl ketal.

For example, the process may further comprise a step of
i) separating the obtained aryl oxirane or α-functionalized alkyl aryl ketal from the organic phase, and/or
ii) taking up the obtained aryl oxirane or α-functionalized alkyl aryl ketal in water and extracting the obtained aqueous phase with an organic solvent.

In one embodiment, the process further comprises the steps of i) separating the obtained aryl oxirane or α-functionalized alkyl aryl ketal from the organic phase, and
ii) taking up the obtained aryl oxirane or α-functionalized alkyl aryl ketal in water and extracting the obtained aqueous phase with an organic solvent.

Additionally, the process may further comprise a step of drying the obtained aryl oxirane or α-functionalized alkyl aryl ketal.

It is appreciated that the aryl oxirane or α-functionalized alkyl aryl ketal obtained by the process can be further reacted to the corresponding α-functionalized ketone.

In one embodiment, the process of the present invention thus comprises a further step of contacting the aryl oxirane obtained by the process under phase-transfer conditions with a base selected from the group comprising alkali metal hydroxide, earth alkali metal hydroxide, alkali metal $C_1$-$C_8$-alkoxide, earth alkali metal $C_1$-$C_8$-alkoxide and mixtures and the a compound selected from $HOR_9$, $HNHR_9$ or $HNR_{10}R_{11}$ with $R_9$, $R_{10}$ and $R_{11}$ being independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_6$-$C_{14}$-aryl, $C_7$-$C_{15}$-arylalkyl, $C_7$-$C_{15}$-arylalkoxy, $C_9$-$C_{15}$-alkenylarylalkoxy, $C_9$-$C_{15}$-alkenylarylalkyl; or $R_{10}$ and $R_{11}$ form a $C_3$-$C_9$-alicyclic system together with the connecting N or C atom, optionally one or more carbon atoms are replaced with O, resulting thereby in the corresponding α-functionalized ketone.

If an α-functionalized ketone is to be prepared from the aryl oxirane, it is thus required that the process is carried out under phase-transfer conditions. Such phase-transfer conditions are well known in the art such that the skilled person will easily apply reaction conditions that are suitable for the reaction mentioned. The skilled person can also apply variants of such reactions which are known per se and are not mentioned herein in detail.

In particular, the reaction of the aryl oxirane is carried out in the presence of a phase-transfer catalyst with the base selected from the group comprising alkali metal hydroxide, earth alkali metal hydroxide, alkali metal $C_1$-$C_8$-alkoxide, earth alkali metal $C_1$-$C_8$-alkoxide and mixtures and the compound selected from $HOR_9$, $HNHR_9$ or $HNR_{10}R_{11}$ with $R_9$, $R_{10}$ and $R_{11}$ being independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_6$-$C_{14}$-aryl, $C_7$-$C_{15}$-arylalkyl, $C_7$-$C_{15}$-arylalkoxy, $C_9$-$C_{15}$-alkenylarylalkoxy, $C_9$-$C_{15}$-alkenylarylalkyl; or $R_{10}$ and $R_{11}$ form a $C_3$-$C_9$-alicyclic system together with the connecting N or C atom, optionally one or more carbon atoms are replaced with O.

The phase-transfer catalyst can be selected from any phase-transfer catalyst known in the art. However, the phase-transfer catalyst is preferably selected from a quaternary ammonium salt, tetraalkylphosphonium chloride, tetraalkylphosphonium bromide and mixtures thereof. More preferably, the phase-transfer catalyst is a tetraalkylammonium salt or a trialkylarylammonium salt, and most preferably the phase-transfer catalyst is selected from the group comprising benzyltrimethylammonium hydroxide, benzyltriethylammonium chloride, tetrabutylammonium chloride, tetrabutylammonium bromide, tetrabutylammonium hydrogensulfate, tetrabutylammonium hydroxide, methyltrioctylammonium chloride, cetyl pyridinium and mixtures thereof Such phase-transfer catalysts are well known in the art such that the skilled person will easily apply catalysts that are suitable for the reaction mentioned. The skilled person can also apply variants of such catalysts which are known per se and are not mentioned herein in detail.

The amount of phase-transfer catalysts can be chosen as desired within wide limits, preferably being 0.1 to 100 wt.-%, based on the weight of the aryl oxirane.

It is preferred that the base is selected from the group comprising sodium hydroxide; potassium hydroxide; sodium $C_1$-$C_6$-alkoxide, preferably sodium $C_1$-$C_4$-alkoxide and most preferably sodium $C_1$-$C_2$-alkoxide; lithium $C_1$-$C_6$-alkoxide, preferably lithium $C_1$-$C_4$-alkoxide and most preferably lithium $C_1$-$C_2$-alkoxide; potassium $C_1$-$C_6$-alkoxide, preferably potassium $C_1$-$C_4$-alkoxide and most preferably potassium $C_1$-$C_2$-alkoxide; and mixtures thereof. Preferably, the base is selected from the group comprising sodium hydroxide and sodium $C_1$-$C_6$-alkoxide, preferably sodium $C_1$-$C_4$-alkoxide and most preferably sodium $C_1$-$C_2$-alkoxide. Most preferably, the base is sodium hydroxide.

The base can be added as such into the process. Alternatively, the base is in form of an aqueous solution or the base is provided in an organic solvent, preferably the organic solvent is selected from the group comprising methanol, ethanol, n-propanol, tert.-butanol, dichloromethane, tetrachloroethylene, tetrahydrofuran, ethyl acetate, acetone, N,N-dimethylformamide, dimethyl sulfoxide, dioxane, such as 1,3-dioxane or 1,4-dioxane, 1,2-dimethoxyethane, diethyleneglycol dimethyl ether, triethyleneglycol dimethyl ether and mixtures thereof. Preferably, the base is provided in form of an aqueous solution.

Another essential component to be added for reacting the obtained aryl oxirane to the corresponding α-functionalized ketone, is a compound selected from $HOR_9$, $HNHR_9$ or $HNR_{10}R_{11}$ with $R_9$, $R_{10}$ and $R_{11}$ being independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_6$-$C_{14}$-aryl, $C_7$-$C_{14}$-arylalkyl, $C_7$-$C_{14}$-arylalkoxy, $C_9$-$C_{15}$-alkenylarylalkoxy, $C_9$-$C_{15}$-alkenylarylalkyl; or $R_{10}$ and $R_{11}$ form a $C_3$-$C_9$-alicyclic system together with the connecting N or C atom, optionally one or more carbon atoms are replaced with O.

In one embodiment, the compound is $HOR_9$ with $R_9$ being selected from linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_7$-$C_{14}$-arylalkoxy and $C_9$-$C_{15}$-alkenylarylalkoxy, preferably $R_9$ is linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl, $C_3$-$C_8$-cycloalkyl, preferably $C_4$-$C_8$-cycloalkyl, more preferably $C_4$-$C_6$-cycloalkyl, and most preferably $C_5$- or $C_6$-cycloalkyl, e.g. $C_6$-cycloalkyl, and $C_6$-$C_{14}$-aryl.

Alternatively, the compound is $HNR_{10}R_{11}$ with $R_{10}$ and $R_{11}$ being independently selected from H, linear or branched $C_1$-$C_8$-alkyl, $C_3$-$C_8$-cycloalkyl, $C_6$-$C_{14}$-aryl, or $R_{10}$ and $R_{11}$ form a $C_3$-$C_6$-alicyclic system together with the connecting N atom, optionally one or more carbon atoms are replaced with O, preferably $R_{10}$ and $R_{11}$ form a $C_5$-$C_6$-alicyclic system together with the connecting N atom and one or more carbon atoms are replaced with O.

Preferably, the compound is $HNR_{10}R_{11}$ with $R_{10}$ and $R_{11}$ forming a $C_5$-$C_6$-alicyclic system, preferably a $C_6$-alicyclic system, together with the connecting N atom and one or more carbon atoms, preferably one carbon atom, is/are replaced with O.

For example, the compound is morpholine.

The further step of reacting the aryl oxirane to the corresponding α-functionalized ketone can be carried out over a wide temperature range. For example, this step is carried out at a temperature of at least 30° C., preferably in the range from 30 to 120° C., more preferably in the range from 40 to 100° C., and most preferably in the range from 40 to 90° C.

It is further appreciated that the further step of reacting the aryl oxirane to the corresponding α-functionalized ketone can be carried out in an organic solvent. Preferably the organic solvent is selected from the group comprising methanol, ethanol, n-propanol, tert.-butanol, dichloromethane, tetrachloroethylene, tetrahydrofuran, ethyl acetate, acetone, N,N-dimethylformamide, dimethyl sulfoxide, dioxane, such as 1,3-dioxane or 1,4-dioxane, 1,2-dimethoxyethane, diethyleneglycol dimethyl ether, triethyleneglycol dimethyl ether and mixtures thereof.

If the base is provided in an organic solvent, the organic solvent is preferably the same as used in the process.

The further step of reacting the aryl oxirane to the corresponding α-functionalized ketone is carried out by mixing the components, i.e. the aryl oxirane, the phase-transfer catalyst, the base selected from the group comprising alkali metal hydroxide, earth alkali metal hydroxide, alkali metal $C_1$-$C_8$-alkoxide, earth alkali metal $C_1$-$C_8$-alkoxide and mixtures and the compound selected from $HOR_9$, $HNHR_9$ or $HNR_{10}R_{11}$ with $R_9$, $R_{10}$ and $R_{11}$ being independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_6$-$C_{14}$-aryl, $C_7$-$C_{14}$-arylalkyl, $C_7$-$C_{14}$-arylalkoxy, $C_9$-$C_{15}$-alkenylarylalkoxy, $C_9$-$C_{15}$-alkenylarylalkyl; or $R_{10}$ and $R_{11}$ form a $C_3$-$C_9$-alicyclic system together with the connecting N or C atom, optionally one or more carbon atoms are replaced with O. The skilled man will adapt the mixing conditions (such as the configuration of mixing tools and mixing speed) according to his process equipment.

It has been found that the sequence of addition of the reagents is unimportant for the success of the reaction. Thus, the aryl oxirane, the phase-transfer catalyst, the base selected from the group comprising alkali metal hydroxide, earth alkali metal hydroxide, alkali metal $C_1$-$C_8$-alkoxide, earth alkali metal $C_1$-$C_8$-alkoxide and mixtures and the compound selected from $HOR_9$, $HNHR_9$ or $HNR_{10}R_{11}$ with $R_9$, $R_{10}$ and $R_{11}$ being independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_6$-$C_{14}$-aryl, $C_7$-$C_{15}$-arylalkyl, $C_7$-$C_{15}$-arylalkoxy, $C_9$-$C_{15}$-alkenylarylalkoxy, $C_9$-$C_{15}$-alkenylarylalkyl; or $R_{10}$ and $R_{11}$ form a $C_3$-$C_9$-alicyclic system together with the connecting N or C atom, optionally one or more carbon atoms are replaced with O, can be contacted in any order.

It is appreciated that the step of reacting the aryl oxirane under phase-transfer conditions with a base selected from the group comprising alkali metal hydroxide, earth alkali metal hydroxide, alkali metal $C_1$-$C_8$-alkoxide, earth alkali metal $C_1$-$C_8$-alkoxide and mixtures and a compound selected from $HOR_9$, $HNHR_9$ or $HNR_{10}R_{11}$ with $R_9$, $R_{10}$ and $R_{11}$ being independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_6$-$C_{14}$-aryl, $C_7$-$C_{15}$-arylalkyl, $C_7$-$C_{15}$-arylalkoxy, $C_9$-$C_{15}$-alkenylarylalkoxy, $C_9$-$C_{15}$-alkenylarylalkyl; or $R_{10}$ and $R_{11}$ form a $C_3$-$C_9$-alicyclic system together with the connecting N or C atom, optionally one or more carbon atoms are replaced with O, results in the corresponding α-functionalized ketone.

Subsequent to the step of reacting the aryl oxirane, the process may comprise further steps for isolating and/or purifying the obtained α-functionalized ketone.

For example, the process may further comprise a step of
i) separating the obtained α-functionalized ketone from the organic phase, and/or
ii) taking up the obtained α-functionalized ketone in water and extracting the obtained aqueous phase with an organic solvent.

In one embodiment, the process further comprises the steps of
i) separating the obtained α-functionalized ketone from the organic phase, and
ii) taking up the obtained α-functionalized ketone in water and extracting the obtained aqueous phase with an organic solvent.

Additionally, the process may further comprise a step of drying the obtained α-functionalized ketone.

Alternatively, the process comprises a further step of contacting the α-functionalized alkyl aryl ketal obtained by the process with an acid obtaining thereby the corresponding α-functionalized ketone.

It is appreciated that the acid is not restricted to a specific acid, but it is preferred that the acid has a pKa value below 5, more preferably in the range from −10 to 10, and most preferably in the range from −8 to 5.

In one embodiment, the acid is preferably selected from the group comprising hydrochloric acid, acetic acid, phosphoric acid, sulfuric acid, citric acid, toluene sulfonic acid, methane sulfonic acid, chloroacetic acid, trichloroacetic acid, tartaric acid, succinic acid, maleic acid, fumaric acid, lactic acid, malic acid, propionic acid, butyric acid and mixtures thereof. For example, the acid is selected from hydrochloric acid, acetic acid, phosphoric acid, sulfuric acid, citric acid and mixtures thereof. In one embodiment, the acid is hydrochloric acid.

The acid can be added as such into the process. Alternatively, the acid is in form of an aqueous solution or the acid is provided in an organic solvent, preferably the organic solvent is selected from the group comprising methanol, ethanol, n-propanol, tert.-butanol, dichloromethane, tetrachloroethylene, tetrahydrofuran, ethyl acetate, acetone, N,N-dimethylformamide, dimethyl sulfoxide, dioxane, such as 1,3-dioxane or 1,4-dioxane, 1,2-dimethoxyethane, diethyleneglycol dimethyl ether, triethyleneglycol dimethyl ether and mixtures thereof. Preferably, the acid is provided in form of an aqueous solution and thus is in form of a dilute aqueous acid. This is advantageous as the reaction to enol ethers can be avoided.

The subsequent step of reacting the α-functionalized alkyl aryl ketal to the corresponding α-functionalized ketone can be carried out over a wide temperature range. For example, this step is carried out at a temperature in the range from 0 to 120° C., preferably in the range from 12 to 80° C., more preferably in the range from 15 to 50° C., and most preferably in the range from 15 to 30° C.

Preferably, this step is carried out at room temperature, i.e. at a temperature of about 21° C. (±2° C.).

It is further appreciated that the subsequent step of reacting the α-functionalized alkyl aryl ketal to the corresponding α-functionalized ketone can be carried out in an organic solvent. Preferably the organic solvent is selected from the group comprising methanol, ethanol, n-propanol, tert.-butanol, dichloromethane, tetrachloroethylene, tetrahydrofuran, ethyl acetate, acetone, N,N-dimethylformamide, dimethyl sulfoxide, dioxane, such as 1,3-dioxane or 1,4-dioxane, 1,2-dimethoxyethane, diethyleneglycol dimethyl ether, triethyleneglycol dimethyl ether and mixtures thereof.

If the acid is provided in an organic solvent, the organic solvents are preferably the same.

The step of reacting the α-functionalized alkyl aryl ketal to the corresponding α-functionalized ketone is carried out by mixing the components, i.e. the α-functionalized alkyl aryl ketal and the acid and, if present, the organic solvent. The skilled man will adapt the mixing conditions (such as the configuration of mixing tools and mixing speed) according to his process equipment.

It has been found that the sequence of addition of the reagents is important for the success of this reaction step. The best yields are obtained when the α-functionalized alkyl aryl ketal and, if present, the organic solvent are contacted first and the acid is metered in.

Subsequent to the step of reacting the α-functionalized alkyl aryl ketal, the process may comprise further steps for isolating and/or purifying the obtained α-functionalized ketone.

For example, the process may further comprise a step of
i) separating the obtained α-functionalized ketone from the organic phase, and/or
ii) taking up the obtained α-functionalized ketone in water and extracting the obtained aqueous phase with an organic solvent.

In one embodiment, the process further comprises the steps of
i) separating the obtained α-functionalized ketone from the organic phase, and
ii) taking up the obtained α-functionalized ketone in water and extracting the obtained aqueous phase with an organic solvent.

Additionally, the process may further comprise a step of drying the obtained α-functionalized ketone.

It is appreciated that an α-functionalized ketone of the general formula II is obtained by further reacting the aryl oxirane or α-functionalized alkyl aryl ketal,

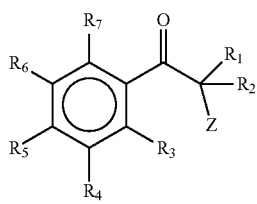

II wherein $R_1$, $R_2$, $R_3$, $R_4$, $R_5$, $R_6$ and $R_7$ are as defined above; and Z is selected from $OR_9$, $NHR_9$ and $NR_{10}R_{11}$ with $R_9$, $R_{10}$ and $R_{11}$ being independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_6$-$C_{14}$-aryl, $C_7$-$C_{15}$-arylalkyl, $C_7$-$C_{15}$-arylalkoxy, $C_9$-$C_{15}$-alkenylarylalkoxy, $C_9$-$C_{15}$-alkenylarylalkyl; or $R_{10}$ and $R_{11}$ form a $C_3$-$C_9$-alicyclic system together with the connecting N or C atom, optionally one or more carbon atoms are replaced with O.

In one embodiment, Z is $OR_9$ with $R_9$ being selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_7$-$C_{15}$-arylalkoxy and $C_9$-$C_{15}$-alkenylarylalkoxy, preferably $R_9$ is H or Z is $NR_{10}R_{11}$ with $R_{10}$ and $R_{11}$ being independently selected from H, linear or branched $C_1$-$C_8$-alkyl, $C_3$-$C_8$-cycloalkyl, $C_6$-$C_{14}$-aryl, or $R_{10}$ and $R_{11}$ form a $C_3$-$C_6$-alicyclic system together with the connecting N atom, optionally one or more carbon atoms are replaced with O, preferably $R_{10}$ and $R_{11}$ form a $C_5$-$C_6$-alicyclic system together with the connecting N atom and one or more carbon atoms are replaced with O.

Preferably, Z is $OR_9$ with $R_9$ being H or $NR_{10}R_{11}$ with $R_{10}$ and $R_{11}$ forming a $C_5$-$C_6$-alicyclic system, preferably a $C_6$-alicyclic system, together with the connecting N atom and one or more carbon atoms, preferably one carbon atom, is/are replaced with O.

With regard to the definition of $R_1$, $R_2$, $R_3$, $R_4$, $R_5$, $R_6$, and $R_7$ and preferred embodiments thereof, reference is made to the statements provided above when discussing the technical details of the process and the alkyl aryl ketone of the general formula I used as starting material in the process of the present invention.

An especially preferred α-functionalized ketone of the general formula II obtained by the process is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_3$, $R_4$, $R_5$, $R_6$ and $R_7$ are the same and are H, and Z is $OR_9$ with $R_9$ being H.

For example, the α-functionalized ketone of the general formula II obtained by the process is a ketone, wherein $R_1$ and $R_2$ are the same and are $C_1$-alkyl; $R_3$, $R_4$, $R_5$, $R_6$ and $R_7$ are the same and are H, and Z is $OR_9$ with $R_9$ being H.

Alternatively, the α-functionalized ketone of the general formula II obtained by the process is a ketone, wherein $R_1$ and $R_2$ form $C_3$-$C_{12}$-cycloalkyl, preferably $C_4$-$C_{10}$-cycloalkyl, more preferably $C_4$-$C_8$-cycloalkyl, even more preferably $C_4$-$C_6$-cycloalkyl, and most preferably $C_5$- or $C_6$-cycloalkyl, e.g. $C_6$-cycloalkyl, together with the connecting C atom; $R_4$, $R_5$, $R_6$ and $R_7$ are the same and are H, and Z is $OR_9$ with $R_9$ being H.

Alternatively, the α-functionalized ketone of the general formula I is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_4$, $R_5$, $R_6$ and $R_7$ are the same and are H, and Z is $NR_{10}R_{11}$ with $R_{10}$ and $R_{11}$ forming a $C_5$-$C_6$-alicyclic system, preferably a $C_6$-alicyclic system.

Alternatively, the α-functionalized ketone of the general formula II obtained by the process is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_4$, $R_5$, $R_6$ and $R_7$ are the same and are H, and Z is $NR_{10}R_{11}$ with $R_{10}$ and $R_{11}$ forming a $C_5$-$C_6$-alicyclic system, preferably a $C_6$-alicyclic system, together with the connecting N atom and one or more, preferably one, carbon atoms are replaced with O.

For example, the α-functionalized ketone of the general formula II obtained by the process is a ketone, wherein $R_1$ and $R_2$ are the same and are $C_1$-alkyl; $R_4$, $R_5$, $R_6$ and $R_7$ are the same and are H, and Z is $NR_{10}R_{11}$ with $R_{10}$ and $R_{11}$ forming a $C_5$-$C_6$-alicyclic system, preferably a $C_6$-alicyclic system, together with the connecting N atom and one or more, preferably one, carbon atoms are replaced with O.

Alternatively, the α-functionalized ketone of the general formula II obtained by the process is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_4$, $R_5$, $R_6$ and $R_7$ are different and one of them, preferably $R_5$, is linear or branched $C_2$-$C_8$-alkenyl, preferably linear or branched $C_2$-$C_6$-alkenyl and most preferably $C_2$-$C_3$-alkenyl, e.g. $C_2$-alkenyl; and the remaining ones are H and Z is $OR_9$ with $R_9$ being H.

For example, the α-functionalized ketone of the general formula II obtained by the process is a ketone, wherein $R_1$ and $R_2$ are the same and are $C_1$-alkyl; $R_4$, $R_5$, $R_6$ and $R_7$ are different and one of them, preferably $R_5$, is linear or branched $C_2$-$C_8$-alkenyl, preferably linear or branched $C_2$-$C_6$-alkenyl and most preferably $C_2$-$C_3$-alkenyl, e.g. $C_2$-alkenyl; and the remaining ones are H and Z is $OR_9$ with $R_9$ being H.

Alternatively, the α-functionalized ketone of the general formula II obtained by the process is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_4$, $R_5$, $R_6$ and $R_7$ are different and one of them, preferably $R_5$, is linear or branched $C_2$-$C_8$-alkenyl, preferably linear or branched $C_2$-$C_6$-alkenyl and most preferably $C_2$-$C_3$-alkenyl, e.g. $C_2$-alkenyl; and the remaining ones are H and Z is $NR_{10}R_{11}$ with $R_{10}$ and $R_{11}$ forming a $C_5$-$C_6$-alicyclic system, preferably a $C_6$-alicyclic system, together with the connecting N atom and one or more, preferably one, carbon atoms are replaced with O.

For example, the α-functionalized ketone of the general formula II obtained by the process is a ketone, wherein $R_1$ and $R_2$ are the same and are $C_1$-alkyl; $R_4$, $R_5$, $R_6$ and $R_7$ are different and one of them, preferably $R_5$, is linear or branched $C_2$-$C_8$-alkenyl, preferably linear or branched $C_2$-$C_6$-alkenyl and most preferably $C_2$-$C_3$-alkenyl, e.g. $C_2$-alkenyl; and the remaining ones are H and Z is $NR_{10}R_{11}$ with $R_{10}$ and $R_{11}$ forming a $C_5$-$C_6$-alicyclic system, preferably a $C_6$-alicyclic system, together with the connecting N atom and one or more, preferably one, carbon atoms are replaced with O.

Alternatively, the α-functionalized ketone of the general formula II obtained by the process is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_4$, $R_5$, $R_6$ and $R_7$ are different and one of them, preferably $R_5$, is $SR_8$ with $R_8$ being selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; and the remaining ones are H and Z is $OR_9$ with $R_9$ being H.

For example, the α-functionalized ketone of the general formula II obtained by the process is a ketone, wherein $R_1$ and $R_2$ are the same and are $C_1$-alkyl; $R_4$, $R_5$, $R_6$ and $R_7$ are different and one of them, preferably $R_5$, is $SR_8$ with $R_8$ being selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; and the remaining ones are H and Z is $OR_9$ with $R_9$ being H.

Alternatively, the α-functionalized ketone of the general formula II obtained by the process is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_4$, $R_5$, $R_6$ and $R_7$ are different and one of them, preferably $R_5$, is $SR_8$ with $R_8$ being selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; and the remaining ones are H and Z is $NR_{10}R_{11}$ with $R_{10}$ and $R_{11}$ forming a $C_5$-$C_6$-alicyclic system, preferably a $C_6$-alicyclic system, together with the connecting N atom and one or more, preferably one, carbon atoms are replaced with O.

For example, the α-functionalized ketone of the general formula II obtained by the process is a ketone, wherein $R_1$ and $R_2$ are the same and are $C_1$-alkyl; $R_4$, $R_5$, $R_6$ and $R_7$ are different and one of them, preferably $R_5$, is $SR_8$ with $R_8$ being selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; and the remaining ones are H and Z is $NR_{10}R_{11}$ with $R_{10}$ and $R_{11}$ forming a $C_5$-$C_6$-alicyclic system, preferably a $C_6$-alicyclic system, together with the connecting N atom and one or more, preferably one, carbon atoms are replaced with O.

Alternatively, the α-functionalized ketone of the general formula II obtained by the process is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_3$, $R_4$, $R_5$, $R_6$ and $R_7$ are different and one of them is $C_2$-$C_8$-alkenyloxy, preferably $C_2$-$C_6$-alkenyloxy and most preferably $C_3$-$C_5$-alkenyloxy, e.g. $C_3$- or $C_4$-alkenyloxy, especially $C_3$-alkenyloxy; and two of the remaining ones are H and two of the remaining ones are linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; and Z is $OR_9$ with $R_9$ being H.

For example, the α-functionalized ketone of the general formula II obtained by the process is a ketone, wherein $R_1$ and $R_2$ are the same and are $C_1$-alkyl; $R_3$, $R_4$, $R_5$, $R_6$ and $R_7$ are different and one of them, preferably $R_5$, is $C_2$-$C_8$-alkenyloxy, preferably $C_2$-$C_6$-alkenyloxy and most preferably $C_3$-$C_5$-alkenyloxy, e.g. $C_3$- or $C_4$-alkenyloxy, especially $C_3$-alkenyloxy; and two of the remaining ones, preferably $R_3$ and $R_7$, are H and two of the remaining ones, preferably $R_4$ and $R_6$, are linear or branched $C_1$-$C_8$-alkyl, e.g. linear $C_1$-$C_8$-alkyl, preferably linear or branched $C_1$-$C_6$- alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl, especially $C_1$-alkyl; and Z is $OR_9$ with $R_9$ being H.

Alternatively, the α-functionalized ketone of the general formula II obtained by the process is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_3$, $R_4$, $R_5$, $R_6$ and $R_7$ are different and three of them, preferably $R_3$ and $R_4$ and $R_5$, are $C_9$-$C_{15}$-alkenylarylalkoxy, preferably $C_9$-$C_{12}$-alkenylarylalkoxy and most preferably $C_9$-$C_{10}$-alkenylarylalkoxy, and the remaining ones, preferably $R_6$ and $R_7$ are H; and Z is $OR_9$ with $R_9$ being H.

For example, the α-functionalized ketone of the general formula II obtained by the process is a ketone, wherein $R_1$ and $R_2$ are the same and are $C_1$-alkyl; $R_3$, $R_4$, $R_5$, $R_6$ and $R_7$ are different and three of them, preferably $R_3$ and $R_4$ and $R_5$, are $C_9$-$C_{15}$-alkenylarylalkoxy, preferably $C_9$-$C_{12}$-alkenylarylalkoxy and most preferably $C_9$-$C_{10}$-alkenylarylalkoxy, and the remaining ones, preferably $R_6$ and $R_7$ are H; and Z is $OR_9$ with $R_9$ being H.

Alternatively, the α-functionalized ketone of the general formula II obtained by the process is a ketone, wherein $R_1$ and $R_2$ are different and are selected from H and linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_3$, $R_4$, $R_5$, $R_6$ and $R_7$ are different and two of them, preferably $R_4$ and $R_5$, are $C_1$-$C_8$-alkoxy, preferably $C_1$-$C_6$-alkoxy and most preferably $C_1$-$C_3$-alkoxy, especially $C_1$-alkoxy; and the remaining ones, preferably $R_3$, $R_6$ and $R_7$, are H and Z is $OR_9$ with $R_9$ being H.

For example, the α-functionalized ketone of the general formula II obtained by the process is a ketone, wherein $R_1$ and $R_2$ are different and are H and $C_2$-alkyl; $R_3$, $R_4$, $R_5$, $R_6$ and $R_7$ are different and two of them, preferably $R_4$ and $R_5$, are $C_1$-$C_8$-alkoxy, preferably $C_1$-$C_6$-alkoxy and most preferably $C_1$-$C_3$-alkoxy, especially $C_1$-alkoxy; and the remaining ones, preferably $R_3$, $R_6$ and $R_7$, are H and Z is $OR_9$ with $R_9$ being H.

Alternatively, the α-functionalized ketone of the general formula II obtained by the process is a ketone, wherein $R_1$ and $R_2$ are different and are selected from H and linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_3$, $R_4$, $R_5$, $R_6$ and $R_7$ are different and one of them, preferably $R_5$, is $N(R_8)_2$ with $R_8$ forming a $C_3$-$C_9$-alicyclic system, preferably a $C_3$-$C_7$-alicyclic system, more preferably a $C_4$-$C_6$-alicyclic system and most preferably a $C_5$- or $C_6$-alicyclic system, together with the connecting N atom, wherein one or more, preferably one, carbon atoms are replaced with O; and the remaining ones, preferably $R_3$, $R_4$, $R_6$ and $R_7$, are H and Z is $OR_9$ with $R_9$ being H.

For example, the α-functionalized ketone of the general formula II obtained by the process is a ketone, wherein $R_1$ and $R_2$ are different and are H and $C_2$-alkyl; $R_3$, $R_4$, $R_5$, $R_6$ and $R_7$ are different and one of them, preferably $R_5$, is $N(R_8)_2$ with $R_8$ forming a $C_3$-$C_9$-alicyclic system, preferably a $C_3$-$C_7$-alicyclic system, more preferably a $C_4$-$C_6$-alicyclic system and most preferably a $C_5$- or $C_6$-alicyclic system, together with the connecting N atom, wherein one or more, preferably one, carbon atoms are replaced with O; and the remaining ones, preferably $R_3$, $R_4$, $R_6$ and $R_7$, are H and Z is $OR_9$ with $R_9$ being H.

Alternatively, the α-functionalized ketone of the general formula II obtained by the process is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_4$ and $R_5$ form an aromatic system together with the benzene ring of general formula I, preferably a bicyclic aromatic system, most preferably naphthyl; and the remaining ones are independently selected from H and linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl, preferably H, and Z is $OR_9$ with $R_9$ being H.

For example, the α-functionalized ketone of the general formula II obtained by the process is a ketone, wherein $R_1$ and $R_2$ are the same and are $C_1$-alkyl; $R_4$ and $R_5$ form an aromatic system together with the benzene ring of general formula I, preferably a bicyclic aromatic system, most preferably naphthyl; and the remaining ones are H and Z is $OR_9$ with $R_9$ being H.

Alternatively, the α-functionalized ketone of the general formula II obtained by the process is a ketone, wherein $R_1$ and $R_2$ are the same and are selected from linear or branched $C_1$-$C_8$-alkyl, e.g. linear $C_1$-$C_8$-alkyl, preferably linear or branched $C_1$-$C_6$-alkyl, e.g. linear $C_1$-$C_6$-alkyl, more preferably linear or branched $C_1$-$C_4$-alkyl, e.g. linear $C_1$-$C_4$-alkyl, and most preferably linear $C_1$-$C_3$-alkyl, e.g. $C_1$- or $C_2$-alkyl, especially $C_1$-alkyl; $R_4$ and $R_5$ form an aromatic system together with the benzene ring of general formula I, preferably a bicyclic aromatic system, most preferably naphthyl; and one of the remaining R, preferably $R_3$, is linear or branched $C_2$-$C_8$-alkenyl, preferably $C_2$-$C_6$-alkenyl and most preferably $C_2$-$C_3$-alkenyl; $C_2$-$C_8$-alkenyloxy, preferably $C_2$-$C_6$-alkenyloxy and most preferably $C_3$-$C_5$-alkenyloxy; and $C_9$-$C_{15}$-alkenylarylalkoxy, preferably $C_9$-$C_{12}$-alkenylarylalkoxy and most preferably $C_9$-$C_{10}$-alkenylarylalkoxy and the remaining ones are H, and Z is $OR_9$ with $R_9$ being H.

For example, the α-functionalized ketone of the general formula II obtained by the process is a ketone, wherein $R_1$ and $R_2$ are the same and are $C_1$-alkyl; $R_4$ and $R_5$ form an aromatic system together with the benzene ring of general formula I, preferably a bicyclic aromatic system, most preferably naphthyl; and one of the remaining R, preferably $R_3$, is $C_9$-$C_{15}$-alkenylarylalkoxy, preferably $C_9$-$C_{12}$-alkenylarylalkoxy and most preferably $C_9$-$C_{10}$-alkenylarylalkoxy and the remaining ones are H, and Z is $OR_9$ with $R_9$ being H.

A further aspect of the present invention refers to the aryl oxirane or α-functionalized alkyl aryl ketal obtained by the process as defined herein.

Accordingly, the aryl oxirane or α-functionalized alkyl aryl ketal are obtained by a process for reacting an alkyl aryl ketone of the general formula I,

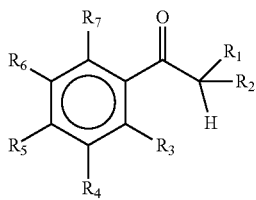

wherein $R_1$ and $R_2$ are the same or different and are independently selected from H, linear or branched $C_1$-$C_8$-alkyl, $C_3$-$C_8$-cycloalkyl, linear or branched $C_2$-$C_8$-alkenyl, $C_5$-$C_8$-cycloalkenyl, linear or branched $C_2$-$C_8$-alkynyl, $C_6$-$C_{14}$-aryl or form $C_3$-$C_{12}$-cycloalkyl or $C_5$-$C_{12}$-cycloalkenyl together with the connecting C atom;

$R_3$, $R_4$, $R_5$, $R_6$ and $R_7$ are the same or different and are independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_6$-$C_{14}$-aryl, $C_3$-$C_8$-cycloalkoxy, $C_7$-$C_{15}$-arylalkoxy, $C_9$-$C_{15}$-alkenylarylalkoxy, $N(R_8)_2$ or $SR_8$ with $R_8$ being selected from linear or branched $C_1$-$C_8$-alkyl, linear or branched $C_2$-$C_8$-alkenyl, $C_6$-$C_{14}$-aryl, $C_1$-$C_8$-alkoxy, $C_2$-$C_8$-alkenyloxy, $C_3$-$C_8$-cycloalkyl, $C_3$-$C_8$-cycloalkoxy, $C_7$-$C_{15}$-arylalkoxy, $C_9$-$C_{15}$-alkenylarylalkoxy, or $R_8$ form a $C_3$-$C_9$-alicyclic system together with the connecting N atom, optionally one or more carbon atoms are replaced with O, or two adjacent R form an aromatic system together with the benzene ring of formula I;

with an at least partially halogenated $C_2$-$C_8$-alkane and/or $C_2$-$C_8$-alkene, and a base selected from alkali metal $C_1$-$C_8$-alkoxide, earth alkali metal $C_1$-$C_8$-alkoxide and mixtures thereof, obtaining thereby the corresponding aryl oxirane or α-functionalized alkyl aryl ketal.

With regard to the definition of the process, $R_1$, $R_2$, $R_3$, $R_4$, $R_5$, $R_6$, and $R_7$ and preferred embodiments thereof, reference is made to the statements provided above when discussing the technical details of the process and the alkyl aryl ketone of the general formula I used as starting material in the process of the present invention.

Another aspect of the present invention refers to the α-functionalized ketone of the general formula II obtained by the process as defined herein.

Accordingly, the α-functionalized ketone of the general formula II is obtained by a process for reacting an alkyl aryl ketone of the general formula I,

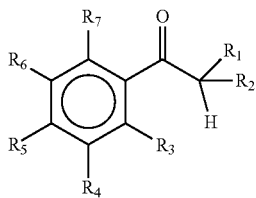

wherein $R_1$ and $R_2$ are the same or different and are independently selected from H, linear or branched $C_1$-$C_8$-alkyl, $C_3$-$C_8$-cycloalkyl, linear or branched $C_2$-$C_8$-alkenyl, $C_5$-$C_8$-cycloalkenyl, linear or branched $C_2$-$C_8$-alkynyl, $C_6$-$C_{14}$-aryl or form $C_3$-$C_{12}$-cycloalkyl or $C_5$-$C_{12}$-cycloalkenyl together with the connecting C atom;

$R_3$, $R_4$, $R_5$, $R_6$ and $R_7$ are the same or different and are independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_6$-$C_{14}$-aryl, $C_3$-$C_8$-cycloalkoxy, $C_7$-$C_{15}$-arylalkoxy, $C_9$-$C_{15}$-alkenylarylalkoxy, $N(R_8)_2$ or $SR_8$ with $R_8$ being selected from linear or branched $C_1$-$C_8$-alkyl, linear or branched $C_2$-$C_8$-alkenyl, $C_6$-$C_{14}$-aryl, $C_1$-$C_8$-alkoxy, $C_2$-$C_8$-alkenyloxy, $C_3$-$C_8$-cycloalkyl, $C_3$-$C_8$-cycloalkoxy, $C_7$-$C_{15}$-arylalkoxy, $C_9$-$C_{15}$-alkenylarylalkoxy, or $R_8$ form a $C_3$-$C_9$-alicyclic system together with the connecting N atom, optionally one or more carbon atoms are replaced with O, or two adjacent R form an aromatic system together with the benzene ring of formula I;

with an at least partially halogenated $C_2$-$C_8$-alkane and/or $C_2$-$C_8$-alkene, and a base selected from alkali metal $C_1$-$C_8$-alkoxide, earth alkali metal $C_1$-$C_8$-alkoxide and mixtures thereof, obtaining thereby the corresponding aryl oxirane, and further contacting the aryl oxirane obtained by the process under phase-transfer conditions with a base selected from the group comprising alkali metal hydroxide, earth alkali metal hydroxide, alkali metal $C_1$-$C_8$-alkoxide, earth alkali metal $C_1$-$C_8$-alkoxide and mixtures and a compound selected from $HOR_9$, $HNHR_9$ or $HNR_{10}R_{11}$ with $R_9$, $R_{10}$ and $R_{11}$ being independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_6$-$C_{14}$-aryl, $C_7$-$C_{15}$-arylalkyl, $C_7$-$C_{15}$-arylalkoxy, $C_9$-$C_{15}$-alkenylarylalkoxy, $C_9$-$C_{15}$-alkenylarylalkyl; or $R_{10}$ and $R_{11}$ form a $C_3$-$C_9$-alicyclic system together with the connecting N or C atom, optionally one or more carbon atoms are replaced with O; obtaining thereby the corresponding α-functionalized ketone.

Alternatively, the α-functionalized ketone of the general formula II is obtained by a process for reacting an alkyl aryl ketone of the general formula I,

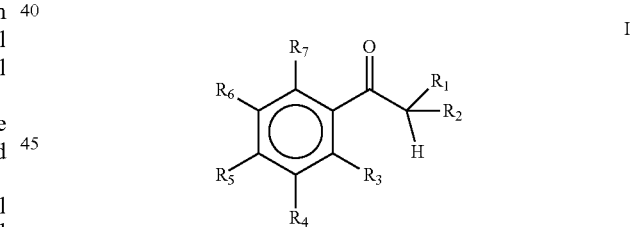

wherein $R_1$ and $R_2$ are the same or different and are independently selected from H, linear or branched $C_1$-$C_8$-alkyl, $C_3$-$C_8$-cycloalkyl, linear or branched $C_2$-$C_8$-alkenyl, $C_5$-$C_8$-cycloalkenyl, linear or branched $C_2$-$C_8$-alkynyl, $C_6$-$C_{14}$-aryl or form $C_3$-$C_{12}$-cycloalkyl or $C_5$-$C_{12}$-cycloalkenyl together with the connecting C atom;

$R_3$, $R_4$, $R_5$, $R_6$ and $R_7$ are the same or different and are independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_6$-$C_{14}$-aryl, $C_3$-$C_8$-cycloalkoxy, $C_7$-$C_{15}$-arylalkoxy, $C_9$-$C_{15}$-alkenylarylalkoxy, $N(R_8)_2$ or $SR_8$ with $R_8$ being selected from linear or branched $C_1$-$C_8$-alkyl, linear or branched $C_2$-$C_8$-alkenyl, $C_6$-$C_{14}$-aryl, $C_1$-$C_8$-alkoxy, $C_2$-$C_8$-alkenyloxy, $C_3$-$C_8$-cycloalkyl, $C_3$-$C_8$-cycloalkoxy, $C_7$-$C_{15}$-arylalkoxy, $C_9$-$C_{15}$-alkenylarylalkoxy, or $R_8$ form a $C_3$-$C_9$-alicyclic system together with the connecting N atom, optionally one or more carbon atoms are replaced with O, or two adjacent R form an aromatic system together with the benzene ring of formula I;

with an at least partially halogenated $C_2$-$C_8$-alkane and/or $C_2$-$C_8$-alkene, and a base selected from alkali metal $C_1$-$C_8$-alkoxide, earth alkali metal $C_1$-$C_8$-alkoxide and mixtures thereof, obtaining thereby the corresponding α-functionalized ketal, and further contacting the α-functionalized alkyl aryl ketal obtained by the process with an acid, preferably an acid selected from the group comprising hydrochloric acid, acetic acid, phosphoric acid, sulfuric acid, citric acid, toluene sulfonic acid, methanesulfonic acid, chloroacetic acid, trichloroacetic acid, tartaric acid, succinic acid, maleic acid, fumaric acid, lactic acid, malic acid, propionic acid, butyric acid and mixtures thereof; obtaining thereby the corresponding α-functionalized ketone.

With regard to the definition of the process, the aryl oxirane, the α-functionalized alkyl aryl ketal the α-functionalized ketone and preferred embodiments thereof, reference is made to the statements provided above when discussing the technical details of the process of the present invention.

The scope and interest of the invention will be better understood based on the following examples which are intended to illustrate certain embodiments of the invention and are non-limitative.

EXAMPLES

Example 1: Preparation of 2-methoxy-3,3-dimethyl-2-(4-methylthiophenyl)oxirane

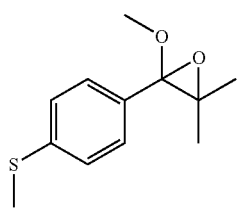

A mixture of sodium methoxide (30% in methanol, 8.34 g, 154 mmol), methanol (15.5 mL), 2-methyl-1-(4-methylthiophenyl)propan-1-one (3.00 g, 15.4 mmol) and hexachloroethane (5.48 g, 23.2 mmol) was stirred overnight at room temperature. The solvent was evaporated, the residue taken up with water (25 mL) and extracted with ethyl acetate (3×20 mL). The combined organic phases were washed with brine (30 mL), dried over $Na_2SO_4$ and the solvent was evaporated. 2-methoxy-3,3-dimethyl-2-(4-methylthiophenyl)oxirane was obtained as a yellow oil (2.86 g, 12.8 mmol, 82% yield).

$^1$H-NMR (400.1 MHz, $CDCl_3$): δ=1.03 (s, 3H), 1.55 (s, 1H), 2.52 (s, 3H), 3.23 (s, 3H), 7.24-7.31 (m, 2H), 7.34-7.43 (m, 2H) ppm.

$^{13}$C-NMR (100.6 MHz, $CDCl_3$): δ=15.5, 19.8, 20.0, 52.6, 67.3, 124.7, 125.8, 128.4, 130.3, 131.4, 139.0 ppm.

Example 2: Preparation of 2-methyl-1-(4-methylthiophenyl)-2-morpholino-propan-1-one

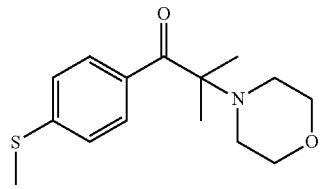 [SMILES: CSc1ccc(C(=O)C(C)(C)N2CCOCC2)cc1]

A mixture of 2-methoxy-3,3-dimethyl-2-(4-methylthiophenyl)oxirane (0.13 g, 0.58 mmol), morpholine (2.27 g, 26.1 mmol), sodium hydroxide solution (50%, 0.28 g, 3.5 mmol) and tetrabutylammonium hydrogensulfate (0.01 g, 0.03 mmol) was stirred under reflux for 8 h. The reaction mixture was cooled down to room temperature, the solvent was evaporated under reduced pressure and the residue was taken up with water (10 mL). The phases were separated and the pH of the aqueous layer was adjusted to 7 with saturated ammonium chloride solution. The aqueous layer was extracted with ethyl acetate (3×5 mL). The combined organic layers were washed with brine (10 mL), dried over $Na_2SO_4$ and the solvent was evaporated. 2-methyl-1-(4-methylthiophenyl)-2-morpholino-propan-1-one was obtained as a colorless oil (70 mg, 0.25 mmol, 43% yield).

$^1$H-NMR (400.1 MHz, $CDCl_3$): δ=1.31 (s, 6H), 2.53 (s, 3H), 2.55-2.61 (m, 4H), 3.66-3.73 (m, 4H), 7.20-7.26 (m, 2H), 8.49-8.54 (m, 2H) ppm. $^{13}$C-NMR (100.6 MHz, $CDCl_3$): δ=14.4, 20.4, 47.2, 67.3, 68.3, 124.3, 130.3, 131.8, 144.9, 201.9 ppm.

Example 3: Preparation of 2,2-diethyl-3-methoxy-3-phenyl-oxirane

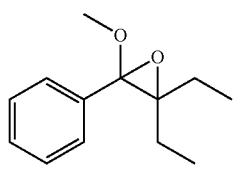

A mixture of sodium methoxide (30% in methanol, 12.3 g, 87.1 mmol), methanol (11.5 mL), 2-ethyl-1-phenylbutan-1-one (2.00 g, 11.4 mmol) and hexachloroethane (2.96 g, 12.5 mmol) was stirred overnight at room temperature. The solvent was evaporated, the residue taken up with water (50 mL) and extracted with ethyl acetate (3×20 mL). The combined organic phases were washed with brine (50 mL), dried over $Na_2SO_4$ and the solvent was evaporated.

The crude product was purified by flash chromatography [basic aluminum oxide, c-$C_6H_{12}$/AcOEt, 1:1 v:v]. 2,2-diethyl-3-methoxy-3-phenyl-oxirane was obtained as a colorless oil (2.26 g, 11.0 mmol, 96% yield).

$^1$H-NMR (400.1 MHz, $CDCl_3$): δ=0.79-0.82 (t, 3H), 1.06-1.10 (t, 3H), 1.16-1.37 (m, 2H), 1.79-1.91 (m, 1H), 1.94-2.04 (m, 1H), 3.21 (s, 3H), 7.34-7.43 (m, 3H), 7.45-7.50 (m, 3H) ppm. $^{13}$C-NMR (100.6 MHz, $CDCl_3$): δ=8.6, 9.3, 22.3, 22.5, 52.4, 73.7, 91.9, 127.9, 128.0, 128.3, 134.9 ppm.

Example 4: Preparation of 4-(1,1-dimethoxy-2-hydroxybutyl)-1,2-dimethoxybenzene

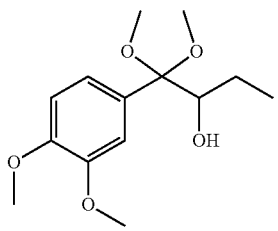 [SMILES: CCC(O)C(OC)(OC)c1ccc(OC)c(OC)c1]

A mixture of sodium methoxide (30% in methanol, 15.82 g, 87.87 mmol), methanol (14.5 mL), 4-butyryl-1,2-dimethoxybenzene (3.00 g, 14.4 mmol) and hexachloroethane (3.79 g, 16.0 mmol) was stirred overnight at room temperature. The solvent was evaporated, the residue taken up with water (25 mL) and extracted with ethyl acetate (3×20 mL). The combined organic phases were washed with brine (30 mL), dried over $Na_2SO_4$ and the solvent was evaporated. 4-(1,1-Dimethoxy-2-hydroxybutyl)-1,2-dimethoxybenzene was obtained as a yellow oil (2.97 g, 10.9 mmol, 79% yield). $^1$H-NMR (400.1 MHz, $CDCl_3$): δ=0.92-0.96 (t, 3H), 0.98-1.11 (m, 1H), 1.46-1.56 (m, 1H), 2.19-2.24 (dd, 1H), 3.24 (s, 3H), 3.36 (s, 3H), 3.77-3.85 (m, 1H), 3.90 (s, 3H), 3.91 (s, 3H), 6.85-6.89 (m, 1H), 6.99-7.06 (m, 2H) ppm. $^{13}$C-NMR (100.6 MHz, $CDCl_3$): δ=10.9, 24.0, 49.3, 49.8, 55.8, 55.9, 76.3, 103.3, 110.3, 111.3, 120.4, 130.3, 148.3, 148.7 ppm.

Example 5: Preparation of 1-(3,4-dimethoxyphenyl)-2-hydroxy-butan-1-one

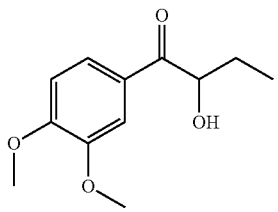 [SMILES: CCC(O)C(=O)c1ccc(OC)c(OC)c1]

1-(3,4-dimethoxyphenyl)-1,1-dimethoxy-butan-2-ol (0.50 g, 1.9 mmol) was dissolved in 1,4-dioxane (8 mL). Hydrochloric acid (1 M, 0.14 g, 3.7 mmol) was added and the reaction mixture was stirred for 6 h at room temperature. Afterwards, the reaction mixture was extracted with ethyl acetate (3×50 mL). The combined organic layers were washed with brine (50 mL) and the solvent was removed under reduced pressure. The crude product was purified by preparative thin layer chromatography on silica gel [c-$C_6H_{12}$/AcOEt, 2:1 v:v]. 1-(3,4-dimethoxyphenyl)-2-hydroxy-butan-1-one was obtained as a colorless oil (0.28 g, 1.0 mmol, 55% yield).

$^1$H-NMR (400.1 MHz, $CDCl_3$): δ=0.94-0.97 (t, 3H), 1.57-1.73 (m, 1H), 1.90-2.01 (m, 1H), 3.73-3.74 (d, 1H), 3.95 (s, 3H), 3.97 (s, 3H), 4.98-5.06 (m, 1H), 6.91-6.95 (m, 1H), 7.51-7.54 (m, 2H) ppm. $^{13}$C-NMR (100.6 MHz, $CDCl_3$): δ=9.0, 29.5, 56.0, 56.1, 73.5, 110.2, 110.6, 123.2, 126.7, 149.4, 154.0, 200.4 ppm.

Example 6: Preparation of 4-(1,1-dimethoxy-2-hydroxybutyl)-phenylmorpholine

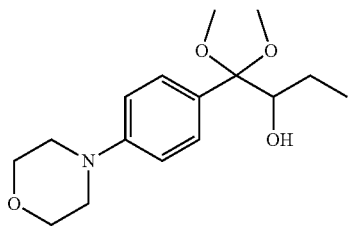 [SMILES: CCC(O)C(OC)(OC)c1ccc(N2CCOCC2)cc1]

A mixture of sodium methoxide (30% in methanol, 4.71 g, 26.1 mmol), methanol (4.5 mL), 4-butyryl-phenylmorpholine (1.00 g, 4.29 mmol) and hexachloroethane (3.79 g, 4.76 mmol) was stirred under reflux for 6 h. The solvent was evaporated, the residue taken up with water (25 mL) and extracted with ethyl acetate (3×20 mL). The combined organic phases were washed with brine (30 mL), dried over $Na_2SO_4$ and the solvent was evaporated. 4-(1,1-Dimethoxy-2-hydroxybutyl)-phenylmorpholine was obtained in as a yellow oil (1.04 g, 3.52 mmol, 92% yield).

$^1$H-NMR (400.1 MHz, $CDCl_3$): δ=0.91-0.95 (t, 3H), 0.96-1.06 (m, 1H), 1.46-1.55 (m, 1H), 3.18-3.22 (m, 5H; two superimposed signals), 3.23 (s, 3H), 3.35 (s, 3H), 3.79-3.84 (m, 1H), 3.87-3.89 (m, 4H), 6.88-6.91 (m, 2H), 7.34-7.39 (m, 2H) ppm.

Example 7: Preparation of 2-hydroxy-1-(4-morpholinophenyl)butan-1-one

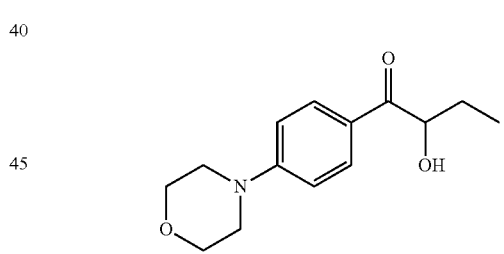

1,1-dimethoxy-1-(4-morpholinophenyl)butan-2-ol (0.50 g, 1.7 mmol) was dissolved in 1,4-dioxane (7.5 mL). Hydrochloric acid (1 M, 0.13 g, 3.4 mmol) was added and the reaction mixture was stirred for 6 h at room temperature. Afterwards, the reaction mixture was extracted with ethyl acetate (3×50 mL). The combined organic layers were washed with brine (50 mL) and the solvent was removed under reduced pressure. 2-hydroxy-1-(4-morpholinophenyl)butan-1-one was obtained as a yellow oil (0.31 g, 1.0 mmol, 60% yield).

$^1$H-NMR (400.1 MHz, $CDCl_3$): δ=0.89-0.92 (t, 3H), 1.53-1.65 (m, 1H), 1.82-1.96 (m, 1H), 3.29-3.31 (m, 4H), 3.42 (wide s, 1H), 3.81-3.83 (m, 4H), 4.91-4.97 (m, 1H), 6.82-6.89 (m, 1H), 7.77-7.86 (m, 2H) ppm. $^{13}$C-NMR (100.6 MHz, $CDCl_3$): δ=8.9, 29.3, 47.4, 66.5, 73.3, 113.1, 122.8, 123.8, 130.3, 130.6, 154.7, 199.7 ppm.

The invention claimed is:
1. A process comprising reacting an alkyl aryl ketone of formula I,

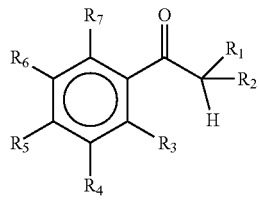

wherein $R_1$ and $R_2$ are the same or different and are independently selected from H, linear or branched $C_1$-$C_8$-alkyl, $C_3$-$C_8$-cycloalkyl, linear or branched $C_2$-$C_8$-alkenyl, $C_5$-$C_8$-cycloalkenyl, linear or branched $C_2$-$C_8$-alkynyl, $C_6$-$C_{14}$-aryl or form $C_3$-$C_{12}$-cycloalkyl or $C_5$-$C_{12}$-cycloalkenyl together with the connecting C atom;

$R_3$, $R_4$, $R_5$, $R_6$ and $R_7$ are the same or different and are independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_6$-$C_{14}$-aryl, $C_3$-$C_8$-cycloalkoxy, $C_7$-$C_{15}$-arylalkoxy, $C_9$-$C_{15}$-alkenylarylalkoxy, $N(R_8)_2$ or $SR_8$ with $R_8$ being selected from linear or branched $C_1$-$C_8$-alkyl, linear or branched $C_2$-$C_8$-alkenyl, $C_6$-$C_{14}$-aryl, $C_1$-$C_8$-alkoxy, $C_2$-$C_8$-alkenyloxy, $C_3$-$C_8$-cycloalkyl, $C_3$-$C_8$-cycloalkoxy, $C_7$-$C_{15}$-arylalkoxy, $C_9$-$C_{15}$-alkenylarylalkoxy, or $R_8$ form a $C_3$-$C_9$-alicyclic system together with the connecting N atom, optionally one or more carbon atoms are replaced with O, or two adjacent residues $R_3$ to $R_7$ form an aromatic system together with the benzene ring of formula I;

by mixing the alkyl aryl ketone of formula I with an at least partially halogenated $C_2$-$C_8$-alkane and/or $C_2$-$C_8$-alkene and a base selected from alkali metal $C_1$-$C_8$-alkoxide, earth alkali metal $C_1$-$C_8$-alkoxide and mixtures thereof, to obtain an aryl oxirane or α-functionalized alkyl aryl ketal;

wherein the at least partially halogenated $C_2$-$C_8$ alkane and/or $C_2$-$C_8$-alkene is hexachloroethane, tetrachloroethylene, pentachloropropane, hexabromoethane, tetrabromoethylene, pentabromopropane, and mixtures thereof.

2. The process according to claim 1, wherein $R_1$ and $R_2$ are the same.

3. The process according to claim 2, wherein $R_1$ and $R_2$ are selected from H and linear or branched $C_1$-$C_8$-alkyl.

4. The process according to claim 1, wherein $R_1$ and $R_2$ are different and are independently selected from H and linear or branched $C_1$-$C_8$-alkyl.

5. The process according to claim 1, wherein $R_1$ and $R_2$ form a $C_4$-$C_{10}$-cycloalkyl together with the connecting C atom.

6. The process according to claim 1, wherein $R_3$, $R_4$, $R_5$, $R_6$ and $R_7$ are the same.

7. The process according to claim 6, wherein $R_3$, $R_4$, $R_5$, $R_6$ and $R_7$ are selected from H and linear or branched $C_1$-$C_8$-alkyl.

8. The process according to claim 1, wherein $R_3$, $R_4$, $R_5$, $R_6$ and $R_7$ are different and at least one of them is selected from linear or branched $C_1$-$C_8$-alkyl, linear or branched $C_2$-$C_8$-alkenyl, $C_1$-$C_8$-alkoxy, $C_2$-$C_8$-alkenyloxy, $C_9$-$C_{15}$-alkenylarylalkoxy or $N(R_8)_2$ or $SR_8$, wherein $R_8$ is selected from linear or branched $C_1$-$C_8$-alkyl or linear or branched $C_2$-$C_8$-alkenyl or $R_8$ form a $C_3$-$C_9$-alicyclic system together with the connecting N atom.

9. The process according to claim 1, wherein one of $R_3$, $R_4$, $R_5$, $R_6$ and $R_7$ is linear or branched $C_2$-$C_8$-alkenyl, $C_1$-$C_8$-alkoxy, $C_2$-$C_8$-alkenyloxy, $C_9$-$C_{15}$-alkenylarylalkoxy or $N(R_8)_2$ or $SR_8$ with $R_8$ being selected from linear or branched $C_1$-$C_8$-alkyl or linear or branched $C_2$-$C_8$-alkenyl or $R_8$ form a $C_3$-$C_9$-alicyclic system together with the connecting N atom; and the remaining ones are independently selected from H and linear or branched $C_1$-$C_8$-alkyl.

10. The process according claim 1, wherein two or three of $R_3$, $R_4$, $R_5$, $R_6$ and $R_7$ are linear or branched $C_2$-$C_8$-alkenyl, $C_1$-$C_8$-alkoxy, $C_2$-$C_8$-alkenyloxy, and $C_9$-$C_{15}$-alkenylarylalkoxy, and the remaining ones are independently selected from H and linear or branched $C_1$-$C_8$-alkyl.

11. The process according to claim 1, wherein $R_3$ and $R_4$ or $R_4$ and $R_5$ form an aromatic system together with the benzene ring of formula I.

12. The process according to claim 11, wherein one of the remaining R is linear or branched $C_2$-$C_8$-alkenyl, $C_2$-$C_8$-alkenyloxy, and $C_9$-$C_{15}$-alkenylarylalkoxy, and the remaining ones are independently selected from H and linear or branched $C_1$-$C_8$-alkyl.

13. The process according to claim 1, wherein the at least partially halogenated $C_2$-$C_8$-alkane and/or $C_2$-$C_8$-alkene is fully halogenated.

14. The process according claim 1, wherein the base is selected from sodium $C_1$-$C_6$-alkoxide, lithium $C_1$-$C_6$-alkoxide, potassium $C_1$-$C_6$-alkoxide, and mixtures thereof.

15. The process according to claim 1, wherein the base is in form of an aqueous solution or the base is provided in an organic solvent.

16. The process according to claim 1, wherein the process is carried out at a temperature in the range from 0 to 120° C.

17. The process according to claim 1, wherein the process is carried out in an organic solvent.

18. The process according to claim 1, wherein the process comprises a further step of contacting the aryl oxirane obtained by the process under phase-transfer conditions with a base selected from alkali metal hydroxide, earth alkali metal hydroxide, alkali metal $C_1$-$C_8$-alkoxide, earth alkali metal $C_1$-$C_8$-alkoxide and mixtures thereof and a compound selected from $HOR_9$, $HNHR_9$ or $HNR_{10}R_{11}$ with $R_9$, $R_{10}$ and $R_{11}$ being independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_6$-$C_{14}$-aryl, $C_7$-$C_{15}$-arylalkyl, $C_7$-$C_{15}$-arylalkoxy, $C_9$-$C_{15}$-alkenylarylalkoxy, $C_9$-$C_{15}$-alkenylarylalkyl; or $R_{10}$ and $R_{11}$ form a $C_3$-$C_9$-alicyclic system together with the connecting N or C atom, optionally one or more carbon atoms are replaced with O.

19. The process according to claim 18, wherein the step is carried out in the presence of a phase-transfer catalyst.

20. The process according to claim 1, wherein the process comprises a further step of contacting the α-functionalized alkyl aryl ketal obtained by the process with an acid.

21. The process according to claim 18, wherein an alkyl aryl ketone of formula II is obtained,

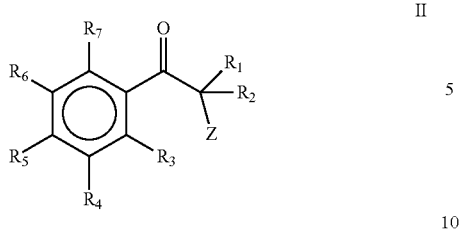

II wherein $R_1$, $R_2$, $R_3$, $R_4$, $R_5$, $R_6$ and $R_7$ are as defined above; and Z is selected from $OR_9$, $NHR_9$ and $NR_{10}R_{11}$ with $R_9$, $R_{10}$ and $R_{11}$ being independently selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_6$-$C_{14}$-aryl, $C_7$-$C_{15}$-arylalkyl, $C_7$-$C_{15}$-arylalkoxy, $C_9$-$C_{15}$-alkenylarylalkoxy, $C_9$-$C_{15}$-alkenylarylalkyl; or $R_{10}$ and $R_{11}$ form a $C_3$-$C_9$-alicyclic system together with the connecting N or C atom, optionally one or more carbon atoms are replaced with O.

22. The process according to claim 21, wherein Z is $OR_9$ with $R_9$ being selected from H, linear or branched $C_1$-$C_8$-alkyl, linear or branched $C_2$-$C_8$-alkenyl, $C_1$-$C_8$-alkoxy, $C_2$-$C_8$-alkenyloxy, $C_3$-$C_8$-cycloalkyl, $C_3$-$C_8$-cycloalkoxy, $C_7$-$C_{15}$-arylalkoxy and $C_9$-$C_{15}$-alkenylarylalkoxy, or Z is $NR_{10}R_{11}$ with $R_{10}$ and $R_{11}$ being independently selected from H, linear or branched $C_1$-$C_8$-alkyl, $C_3$-$C_8$-cycloalkyl, $C_6$-$C_{14}$-aryl, or $R_{10}$ and $R_{11}$ form a $C_3$-$C_6$-alicyclic system together with the connecting N atom, optionally one or more carbon atoms are replaced with O.

\* \* \* \* \*